US008518436B2

(12) United States Patent
Voytik-Harbin

(10) Patent No.: US 8,518,436 B2
(45) Date of Patent: Aug. 27, 2013

(54) ENGINEERED EXTRACELLULAR MATRICES

(75) Inventor: Sherry L. Voytik-Harbin, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 684 days.

(21) Appl. No.: 11/914,606

(22) PCT Filed: May 16, 2006

(86) PCT No.: PCT/US2006/018998
§ 371 (c)(1),
(2), (4) Date: Nov. 16, 2007

(87) PCT Pub. No.: WO2006/124946
PCT Pub. Date: Nov. 23, 2006

(65) Prior Publication Data
US 2009/0011021 A1  Jan. 8, 2009

Related U.S. Application Data

(60) Provisional application No. 60/681,278, filed on May 16, 2005, provisional application No. 60/681,511, filed on May 16, 2005, provisional application No. 60/681,689, filed on May 16, 2005.

(51) Int. Cl.
*A61F 13/00* (2006.01)
*A61K 38/17* (2006.01)
*C07K 1/00* (2006.01)
*C07K 14/00* (2006.01)
*C07K 16/00* (2006.01)
*C07K 17/00* (2006.01)
*C09H 1/00* (2006.01)

(52) U.S. Cl.
USPC ........................................................ 424/443

(58) Field of Classification Search
USPC .......................................... 424/443; 530/356
See application file for complete search history.

(56) References Cited

U.S. PATENT DOCUMENTS

| | | | |
|---|---|---|---|
| 3,949,073 A | 4/1976 | Daniels et al. | |
| 4,233,360 A | 11/1980 | Luck et al. | |
| 4,544,516 A | 10/1985 | Hughes et al. | |
| 4,582,640 A | 4/1986 | Smestad et al. | |
| 4,789,663 A | 12/1988 | Wallace et al. | |
| 4,902,508 A | 2/1990 | Badylak et al. | |
| 4,956,178 A | 9/1990 | Badylak et al. | |
| 5,163,955 A | 11/1992 | Love et al. | |
| 5,204,382 A | 4/1993 | Wallace et al. | |
| 5,275,826 A | 1/1994 | Badylak et al. | |
| 5,281,422 A | 1/1994 | Badylak et al. | |
| 5,420,248 A | 5/1995 | Devictor et al. | |
| 5,460,962 A * | 10/1995 | Kemp ........................... | 435/238 |
| 5,554,389 A | 9/1996 | Badylak et al. | |
| 5,885,619 A | 3/1999 | Patel et al. | |
| 5,948,429 A | 9/1999 | Bell et al. | |
| 5,955,110 A | 9/1999 | Patel et al. | |
| 6,099,567 A | 8/2000 | Badylak et al. | |
| 6,187,047 B1 * | 2/2001 | Kwan et al. ................. | 623/16.11 |
| 6,206,931 B1 | 3/2001 | Cook et al. | |
| 6,264,992 B1 | 7/2001 | Voytik-Harbin et al. | |
| 6,375,989 B1 | 4/2002 | Badylak et al. | |
| 6,384,196 B1 | 5/2002 | Weis et al. | |
| 6,444,229 B2 | 9/2002 | Voytik-Harbin et al. | |
| 6,497,875 B1 | 12/2002 | Sorrell et al. | |
| 6,576,265 B1 | 6/2003 | Spievack | |
| 6,592,623 B1 | 7/2003 | Bowlin et al. | |
| 6,592,794 B1 | 7/2003 | Bachrach | |
| 6,666,892 B2 | 12/2003 | Hiles et al. | |
| 6,793,939 B2 | 9/2004 | Badylak | |
| 6,893,812 B2 | 5/2005 | Woltering et al. | |
| 7,029,689 B2 | 4/2006 | Berglund et al. | |
| 2002/0076816 A1 | 6/2002 | Dai et al. | |
| 2002/0170120 A1 | 11/2002 | Eckmayer et al. | |
| 2002/0172705 A1 | 11/2002 | Murphy et al. | |
| 2004/0037813 A1 | 2/2004 | Simpson et al. | |
| 2004/0078076 A1 | 4/2004 | Badylak et al. | |
| 2004/0137616 A1 | 7/2004 | Isseroff et al. | |
| 2005/0014181 A1 | 1/2005 | Galis et al. | |
| 2005/0019419 A1 | 1/2005 | Badylak et al. | |
| 2005/0153442 A1 | 7/2005 | Katz et al. | |
| 2005/0226856 A1 | 10/2005 | Ahlfors | |
| 2005/0260748 A1 | 11/2005 | Chang et al. | |
| 2005/0266556 A1 | 12/2005 | Yoder et al. | |

(Continued)

FOREIGN PATENT DOCUMENTS

| | | |
|---|---|---|
| DE | 201 15 753 U1 | 1/2002 |
| EP | 0443094 | 8/1991 |

(Continued)

OTHER PUBLICATIONS

"Basement Membrane" accessed online at http://en.wikipedia.org/wiki/Basement_membrane#Composition on Jun. 11, 2010.*
"Extracellular Matrix" accessed online at http://en.wikipedia.org/wiki/Extracellular_matrix on Jun. 11, 2010.*
"Density" from Merriam-Webster online, accessed on Feb. 1, 2011.*
Munakata et al. Glycobiology, 9(10): 1023-1027, 1999.*
Liu et al., Asian-Aust. J. Anim. Sci., 14(11): 1638-1644, 2001.*
International Preliminary Report on Patentability for PCT/US2006/018998 issued Nov. 20, 2007.

(Continued)

*Primary Examiner* — Thaian N Ton
(74) *Attorney, Agent, or Firm* — Barnes & Thornburg LLP

(57) ABSTRACT

The invention relates to engineered matrices comprising collagen fibrils with specific characteristics, including, but not limited to, a specific fibril area fraction (i.e., density) and/or a specific elastic or linear modulus (i.e., stiffness). The invention also relates to methods of preparation and use of the matrices.

39 Claims, 8 Drawing Sheets

(56) References Cited

U.S. PATENT DOCUMENTS

| | | |
|---|---|---|
| 2006/0147501 A1 | 7/2006 | Hillas et al. |
| 2006/0165667 A1 | 7/2006 | Laughlin et al. |
| 2006/0235511 A1 | 10/2006 | Osborne |
| 2007/0026518 A1 | 2/2007 | Healy et al. |
| 2007/0077652 A1 | 4/2007 | Peled et al. |
| 2008/0025956 A1 | 1/2008 | Yoder et al. |
| 2008/0107750 A1 | 5/2008 | Hodde et al. |
| 2012/0027732 A1 | 2/2012 | Voytik-Harbin |
| 2012/0115222 A1 | 5/2012 | Voytik-Harbin et al. |
| 2012/0141417 A1 | 6/2012 | Voytik-Harbin et al. |

FOREIGN PATENT DOCUMENTS

| | | |
|---|---|---|
| EP | 1264878 | 12/2002 |
| EP | 1 270 672 | 1/2003 |
| EP | 1 674 116 | 6/2006 |
| GB | 2366736 | 3/2002 |
| JP | 07 074239 B | 8/1995 |
| WO | WO 94/03119 | 2/1994 |
| WO | WO01/23529 | 4/2001 |
| WO | WO01/45765 | 6/2001 |
| WO | WO 02/102237 | 12/2002 |
| WO | WO 03/068287 | 8/2003 |
| WO | WO03/071991 | 9/2003 |
| WO | WO 03/087337 | 10/2003 |
| WO | WO 03/097694 | 11/2003 |
| WO | WO 2004/028404 | 4/2004 |
| WO | WO2004/060426 | 7/2004 |
| WO | WO 2004/078120 | 9/2004 |
| WO | WO 2006/003442 | 1/2006 |

OTHER PUBLICATIONS

Bell, Brett J. et al., "Cell Density and Extracellular Matrix (ECM) Microstructure Control Mechanical Behavior of Engineered Tissue Constructs", *2005 Summer Bioengineering conference*, (Jun. 22-26, 2005).

Bjornsson, S., "Simultaneous Preparation and Quantitation of Proteoglycans by Precipitation with Alcian Blue", Analytical Biochemistry, vol. 210, 1993, pp. 282-291.

Callister, W. D, Jr., Materials Science and Engineering: an Introduction, 3$^{rd}$ edition, New York, NY, John Wiley & Sons, Inc., 1994.

Comper, W. D., and A. Veis, "Characterization of Nuclei in in Vitro Collagen Fibril Formation", Biopolymers, vol. 16, 1977, pp. 2133-2142.

Davis, et al., "Injectable Self-Assembling Peptide Nanofibers Create Intramyocardial Microenvironments for Endothelial Cells", *Circulation*, 111, 442-50, (Feb. 1, 2005).

Gallop, P. M., and S. Seifter, "Preparation and Properties of Soluble Collagens", Soluble Collagens, 1963, pp. 635-641.

Hou, et al., "Radiolabeled Cell Distribution After Intramyocardial, Intracoronary, and Interstitial Retrograde Coronary Venous Delivery", *Circulation*, 112, 150-6, (Aug. 30, 2005).

Ingram, D. A., et al., "Identification of a Novel Hierarchy of Endothelial Progenitor Cells Using Human Peripheral and Umbilical Cord Blood", Blood, 104, 2752-2760, (2004).

Lin et al., "Comparison of Physical-Chemistry Properties of Type I Collagen from Different Species," *Food Chemistry*, 99(2): 244-251 (2006), available online Sep. 21, 2005.

Malvern, *Introduction to the Mechanics of a Continuous Medium*. Upper Saddle River, NJ: Prentice-Hall, 1969.

Marotta, M., G. Martino, "Sensitive Spectrophotometric Method for the Quantitative Estimation of Collagen", Analytical Biochemistry, vol. 150, 1985, pp. 86-90.

Miller et al., "Preparation and Characterization of the Different Types of Collagen," *Methods in Enzymology*, 82: 33-64 (1982).

Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research.

Narmoneva et al., "Endothelial Cells Promote Cardiac Myocyte Survival and Spatial Reorganization", *Circulation*, 110, 962-968, (Aug. 24, 2004).

Nguyen et al., "Comparison of the Amino Acid Composition of Two Commercial Porcine Skins (Rind)," *Journal of Agricultural and Food Chemistry*, 34(3): 565-572 (1986).

Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.

Osborne, et al., "Investigation into the tensile properties of collagen/chondroitin-6-sulphate gels: the effect of crosslinking agents and diamines", *Medical & Biological Engineering & Computing*, vol. 36, 129-134, (1998).

Ozerdem, et al., "Physical Response of Collagen Gels to Tensile Strain", *Journal of Biomechanical Engineering*, vol. 117, 397-401, (Nov. 1995).

Pizzo et al., "Cell-Extracellular Matrix (ECM) Micro-Mechanical Behavior Depends on ECM Microstructure and Cell Type", *2005 Summer Bioengineering Conference*, (Jun. 22-26, 2005).

Rehman, et al., "Secretion of Angiogenic and Antiapoptotic Factors by Human Adipose Stromal Cells", *Circulation*, 109: 1292-8, (Mar. 16, 2004).

Reinlib, et al., "Cell Transplantation as Future Therapy for Cardiovascular Disease?", *Circulation*, 101: e182-e187, (2000).

Roeder et al., "Local, Three-Dimensional Strain Measurements Within Largely Deformed Extracellular Matrix Constructs", *J Biomech Eng*, 126, 699-708, (2004).

Strang, et al., *Linear Algebra and Its Applications*. 3rd edition. San Diego, CA: Academic Press, 1988.

Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.

Veis, Arthur, et al., "Fundamentals of Interstitial Collagen Self-Assembly", 1994, Extracellular Matrix Assembly and Structure, Academic Press, pp. 15-45.

Voytik-Harbin et al., "Application and Evaluation of the Alamarblue Assay for Cell Growth and Survival of Fibroblasts", *In Vitro Cell Dev Biol Anim*, 34, 239-246, (1998).

Voytik-Harbin et al., "Simultaneous Mechanical Loading and Confocal Reflection Microscopy for Three-Dimensional Microbiomechanical Analysis of Biomaterials and Tissue Constructs", *Microsc Microanal*, 9, 74-85, (2003).

Voytik-Harbin et al., Small Intestinal Submucosa: A Tissue-Derived Extracellular Matrix That Promotes Tissue-Specific Growth and Differentiation of Cells in Vitro, *Tissue Engineering*, 4, 2, 157-174, (1998).

Voytik-Harbin et al., "Three-Dimensional Imaging of Extracellular Matrix and Extracellular Matrix-Cell Interactions", *Methods in Cell Biology*, 63, 583-597, (2001).

Fulzele, S.V., et al., "Study of the Biodegradation and in Vivo Biocompatibility of Novel Biomaterials", 2003, *European Journal of Pharmaceutical Sciences*, vol. 20, pp. 53-61.

Griffey, Sy, et al., "Particulate Dermal Matrix As an Injectable Soft Tissue Replacement Material", Nov. 21, 2000, John Wiley & Sons, Inc., pp. 10-15.

Hunt, Thomas K., et al., "Respiratory Gas Tensions and pH in Healing Wounds", 1967, American Journal of Surgery, Presented at the Thirty-Eighth Annual Meeting of the Pacific Coast Surgical Association, pp. 302-307.

Pizzo, A.M., et al., "Extracellular Matrix (ECM) Microstructural Composition Regulates Local Cell-ECM Biomechanics and Fundamental Fibroblast Behavior: A Multidimensional Perspective", May 2005, *Journal Applied Physiol.*, vol. 98, pp. 1909-1921.

Roeder, Blayne A. et al., "Tensile Mechanical Properties of Three-Dimensional Type I Collagen Extracellular Matrices With Varied Microstructure", Apr. 2002, *Journal of Biomechanical Engineering*, Transactions of the ASME, vol. 124, pp. 214-222.

Schilling, John H., et al., "Wound Healing: A Comparative Study of the Histochemical Changes in Granulation Tissue Contained in Stainless Steel Wire Mesh and Polyvinyl Sponge Cylinders", Oct. 1959, *Surgery*, vol. 46, No. 4, pp. 702-710.

International Search Report and Written Opinion for PCT/US2006/018998 filed May 16, 2006.

Brightman, A.O., et al., "Time-Lapse Confocal Reflection Microscopy of Collagen Fibrillogenesis and Extracellular Matrix Assembly in Vitro", Apr. 3, 2000, Biopolymers, vol. 54, pp. 222-234.

Na et al., "In Vitro Collagen Fibril Assembly in Glycerol Solution: Evidence for a Helical Cooperative Mechanism Involving Microfibrils," Biochemistry, 1986; 25: 958-966.

Na et al., "Mechanism of in Vitro Collagen Fibril Assembly," Journal of Biological Chemistry, 1986; 261(26): 12290-12299.

Voytik-Harbin et al., "Identification of Extractable Growth Factors from Small Intestine Submucosa," J Cell. Biochemistry, 1997; 67: 478-491.

Condell RA et al., "Analysis of Native Collagen Monomers and Oligomers by Size-Exclusion High-Performance Liquid Chromatography and its Application," *Analytical Biochemistry*, 1993; 212: 436-445.

Kim, "Characterization of Acid-soluble Collagen from Pacific Whiting Surimi Processing Byproducts," J. Food Science, 2004, 69: C637-C642.

Billiar, Cellular and Biomolecular Mechanics and Mechanobiology, Amit Gefen, Ed., p. 210 (2011).

Sieminski et al., Expt. Cell Res., vol. 297, pp. 574-584 (2004).

Korff et al., Jour. of Cell Science, vol. 112: 3249-3258 (1999).

Ho et al., "Characterization of Collagen Isolation and Application of Collagen Gel as a Drug Carrier", J. of Controlled Release, vol. 44, pp. 103-112 (1997).

Lynn et al., "Antigenicity and immunogenicity of collagen," J Biomed Mater Res, Part B: Appl Biomater, 2004; 71B: 343-354.

Brennan and Davison, "Role of aldehydes in collagen fibrillogenesis in vitro," Biopolymers, vol. 19, 1980, Issue 10. p. 1861-1873.

Compston, "Bone marrow and bone: a functional unit," Journal of Endocrinology, 173: 387-394, 2002.

Gelman et al., "Collagen Fibril Formation in Vitro," J. Biol. Chem., 1979, 254(22): 11741-11745.

Gelman et al., "Collagen Fibril Formation," J. Biol. Chem., 1979, 254(1):180-186.

Kacena et al., J. of Histotechnology, 2004, 27:119-130.

Knott et al., "Collagen Cross-Links in Mineralizing Tissues: A Review of Their Chemistry, Function, and Clinical Relevance." 1998. 22(31:181-187.

Kondo et al., "Biology of Hematopoietic Stem Cells and Progenitors: Implications for Clinical Application." Annu. Rev. Immunol., 2003, 21:759-806.

Na, "Monomer and Oligomer of Type I Collagen: Molecular Properties and Fibril Assembly," 1989, 28(18):7161-67.

Orschell-Traycoff et al., Blood, 2000, 96:1380-1387.

Pizzo et al., "Long-term Production of Choline Acetylatransferase in the CNS After Transplantation of Fibroblasts Modified with a Regulatable Vector". *Mol. Brain Res*. 126. 1-13 (2004).

Schechner et al., "In vivo formation of complex microvessels lined by human endothelial cells in an immunodeficient mouse," *PNAS*, Aug. 1, 2000, vol. 97, No. 16, 9191-9196.

Spradling et al., "Stem Cells Find Their Niche," Nature, 414: 98-104, 2001.

Taichman et al., "Human Osteoblasts Support Hematopoiesis through the Production of Granulocyte Colony-stimulating Factor," Journal of Experimental Medicine, 1994; 179:1677-1682.

* cited by examiner

ENGINEERED EXTRACELLULAR MATRICES

CROSS-REFERENCE TO RELATED APPLICATIONS

This application is a U.S. national counterpart application of international application serial no. PCT/US2006/018998 filed May 16, 2006, which claims priority under 35 U.S.C. §119(e) to U.S. Provisional Application Ser. Nos. 60/681,278; 60/681,511; and 60/681,689, all filed on May 16, 2005. The disclosure of each of these provisional applications is incorporated herein by reference.

GOVERNMENT RIGHTS

This invention was made with government support under Grant No. EB000165 awarded by the National Institute of Health and Grant No. EEC-0353901 awarded the National Science Foundation. The government has certain rights in the invention.

FIELD OF THE INVENTION

This invention relates to the preparation of engineered matrices derived from solubilized extracellular matrix components from extracellular matrix material of a warm-blooded vertebrate, or derived from purified collagen. The invention also relates to the resulting engineered matrices.

BACKGROUND AND SUMMARY

The interaction of cells with their extracellular matrix in the in vivo environment plays a crucial role in the organization, homeostasis, and function of tissues and organs. Continuous communication between cells and their surrounding extracellular matrix environment orchestrates critical processes such as the acquisition and maintenance of differentiated phenotypes during embryogenesis, the development of form (morphogenesis), angiogenesis, wound healing, and even tumor metastasis. Both biochemical and biophysical signals from the extracellular matrix modulate fundamental cellular activities including adhesion, migration, proliferation, differential gene expression, and programmed cell death.

In turn, the cell can modify its extracellular matrix environment by modulating the synthesis and degradation of specific matrix components. The realization of the significance of cell-extracellular matrix interaction has led to a renewed interest in characterizing extracellular matrix constituents and the basic mechanisms of cell-extracellular matrix interaction.

Various basement membrane tissues and other extracellular matrix tissues can be utilized as tissue graft constructs for remodeling tissues in vivo or for in vitro applications. Complex scaffolds representing combinations of extracellular matrix components in a natural or processed form are commercially available and can also be used for remodeling tissues in vivo or for in vitro applications. For example, extracellular matrices such as Human Extracellular Matrix (Becton Dickinson) and MATRIGEL® are commercially available. Basement membrane tissues and other extracellular tissues, such as submucosa tissues, harvested from warm blooded vertebrates have also shown great promise as unique graft materials for inducing the repair of damaged or diseased tissues in vivo, and for inducing the proliferation of cell populations in vitro.

For example, submucosa tissue constructs are characterized by excellent mechanical properties, including high compliance, high tensile strength, a high burst pressure point, and tear-resistance, while offering additional advantages such as resistance to infection, lack of immunogenicity, and stability. Furthermore, submucosa tissues can be extracted or fluidized or components can be purified from submucosa tissues to provide compositions useful in tissue graft applications. Extracts or fluidized preparations or purified extracellular matrix components can be utilized as additives for tissue culture media to promote in vitro cell growth and proliferation, and can also be used as active ingredients for other tissue graft compositions, such as wound healing compositions.

As a tissue graft material, submucosa tissue undergoes remodeling and induces the growth of endogenous tissues upon implantation into a host. Numerous studies have shown that submucosa tissue is capable of inducing host tissue proliferation, remodeling, and regeneration of tissues following implantation in a number of in vivo environments, including the urinary tract, the body wall, tendons, ligaments, bone, cardiovascular tissues, and other vascular tissues, and the central nervous system. Submucosa tissue has been used successfully, for example, in vascular grafts, for urinary bladder repair, for hernia repair, for replacement and repair of tendons and ligaments, for body wall repair, as a vaginal sling, for rotator cuff repair, for wound care and management, and as a dermal graft. Upon implantation of the submucosa tissues, cellular infiltration and rapid neovascularization are observed and the submucosa materials are remodeled into host replacement tissue with site-specific structural and functional properties.

Accordingly, submucosa tissue can be used as a tissue graft construct, for example, in its native form, in its fluidized form, in the form of an extract, or as components extracted from or solubilized from submucosa tissue and subsequently purified. The fluidized forms of vertebrate submucosa tissue can be gelled to form a semi-solid composition that can be implanted as a tissue graft construct or utilized as a cell culture substrate. As a tissue graft material, the fluidized form of submucosa tissue can be injected, or delivered using other methods, to living tissues to enhance tissue remodeling. Furthermore, the fluidized form can be modified, or can be combined with specific proteins, growth factors, drugs, vectors, or other therapeutic agents for promoting the enhancement or suppression of tissue remodeling at the site of injection. Moreover, the fluidized form of submucosa tissue can be combined with cells, for example primary cells or cell lines, prior to injection to further enhance the repair or replacement of diseased or damaged tissues.

Applicants have discovered here that the physical state of an extracellular matrix graft construct and molecular composition should be considered in the design of new and improved graft constructs. Modifying the conditions used to form a collagen-based matrix allows for the controlled alteration of the micro-structural and subsequent mechanical properties of the resulting engineered matrix. Furthermore, the micro-structural and mechanical properties of the engineered matrix impact cell behavior including proliferation, migration, and differentiation of cells growing on or within the matrix. The engineered matrices of the present invention are distinguished from previously prepared amorphous aggregates of collagen because the engineered matrices described herein comprise collagen fibrils with specific characteristics, including, but not limited to, a specific fibril area fraction (i.e., density) and/or a specific elastic or linear modulus (i.e., stiffness). The engineered matrices described herein can also be made under conditions, where, for example, collagen concentration is controlled.

In one illustrative aspect, a kit is provided. The kit comprises a three-dimensional, engineered matrix comprising collagen fibrils wherein the fibril area fraction of the matrix is about 7% to about 26%. In various illustrative embodiments, the matrix comprises purified collagen or solubilized extracellular matrix components, the matrix is lyophilized, the kit comprises instructional materials for use of the matrix wherein the instructional materials include instructions for injection of the matrix into a patient and/or instructions for growth of cells on the matrix, and the matrix further comprises particulate extracellular matrix material for bulking. In other illustrative kit embodiments, the solubilized extracellular matrix components comprise components from vertebrate submucosa tissue, or basement membrane tissue.

In another embodiment a kit is provided. The kit comprises a three-dimensional, engineered matrix comprising collagen fibrils wherein the elastic or linear modulus of the matrix is about 0.5 to about 40 kPa. In various illustrative embodiments, the matrix comprises purified collagen or solubilized extracellular matrix components, the matrix is lyophilized, the kit comprises instructional materials for use of the matrix wherein the instructional materials include instructions for injection of the matrix into a patient and/or instructions for growth of cells on the matrix, and the matrix further comprises particulate extracellular matrix material for bulking. In other illustrative kit embodiments, the solubilized extracellular matrix components comprise components from vertebrate submucosa tissue, or basement membrane tissue.

In yet another embodiment, a kit is provided for preparing three-dimensional engineered matrices comprising collagen fibrils. The kit comprises a vessel comprising purified collagen or solubilized extracellular matrix components, a glucose solution, a calcium chloride solution, an acid solution selected from the group consisting of HCl, formic acid, sulfuric acid, ethanoic acid, carbonic acid, nitric acid, or phosphoric acid, and a neutralizing solution.

In still another illustrative embodiment, a method of enhancing the repair of tissues in a warm-blooded vertebrate is provided. The method comprises the steps of providing a three-dimensional, engineered matrix comprising collagen fibrils wherein the fibril area fraction of the matrix is about 7% to about 26%, and injecting the matrix into a desired site of said vertebrate.

In another aspect, a method of enhancing the repair of tissues in a warm-blooded vertebrate is provided. The method comprises the steps of providing a three-dimensional, engineered matrix comprising collagen fibrils wherein elastic or linear modulus of the matrix is about 0.5 to about 40 kPa, and injecting the matrix into a desired site of said vertebrate.

In another embodiment, a method is provided of preparing a three-dimensional, engineered matrix comprising collagen fibrils wherein the fibril area fraction of the matrix is about 7% to about 26%. The method comprises the steps of providing purified collagen or solubilized extracellular matrix components, and polymerizing the purified collagen or solubilized extracellular matrix components into fibrils by systematically varying the polymerization conditions. In this embodiment, the polymerization conditions are selected from the group consisting of pH, phosphate concentration, temperature, buffer composition, ionic strength, the solubilized extracellular matrix components polymerized, and concentration of the solubilized extracellular matrix components.

In another embodiment, a method is provided of preparing a three-dimensional, engineered matrix comprising collagen fibrils wherein the elastic or linear modulus of the matrix is about 0.5 to about 40 kPa. The method comprises the steps of providing purified collagen or solubilized extracellular matrix components, and polymerizing the purified collagen or solubilized extracellular matrix components into fibrils by systematically varying the polymerization conditions. In this embodiment, the polymerization conditions are selected from the group consisting of pH, phosphate concentration, temperature, buffer composition, ionic strength, the solubilized extracellular matrix components polymerized, and concentration of the solubilized extracellular matrix components.

BRIEF DESCRIPTION OF THE DRAWINGS

FIG. 1A shows the effect of polymerization temperature on a matrix formed from a solubilized extracellular matrix composition (small intestinal submucosa tissue (SIS)) comprising 1 mg/mil collagen in 1×PBS at pH 7.4; FIG. 1B shows the effect of the buffer type on a matrix formed from a solubilized extracellular matrix composition (SIS) comprising 1 mg/ml collagen, and about 0.15 M NaCl at 37° C.; FIG. 1C shows the effect of pH (using a phosphate buffer) on a matrix formed from a solubilized extracellular matrix composition (SIS) comprising 1 mg/ml collagen, in 1×PBS at pH 7.4; FIG. 1D shows the effect of pH (using a Tris buffer) on a matrix formed from a solubilized extracellular matrix composition (SIS) comprising 1 mg/ml collagen, in 50 mM Tris, and about 0.15 M NaCl at 37° C.; FIG. 1E shows the effect of ionic strength on a matrix formed from a solubilized extracellular matrix composition (SIS) comprising 1 mg/ml collagen, no buffer, at 37° C.; FIG. 1F shows the effect of phosphate concentration on a matrix formed from a solubilized extracellular matrix composition (SIS) comprising 1 mg/ml collagen, and about 0.15 M NaCl at 37° C.;

DETAILED DESCRIPTION OF THE ILLUSTRATIVE EMBODIMENTS

Figure 1A:
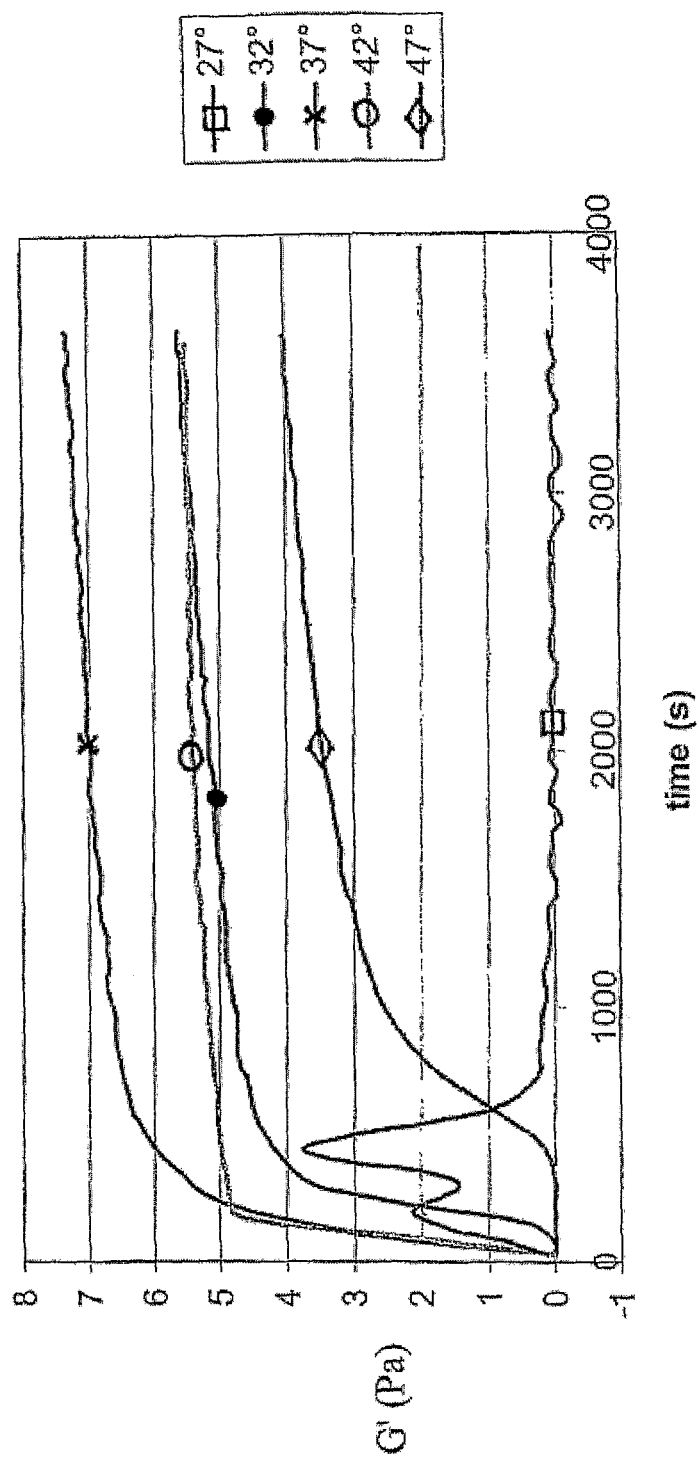
FIGS. 1A-1F present data showing the effect of various parameters on the stiffness (elastic or linear modulus) of the formed matrix.
Figure 1B:
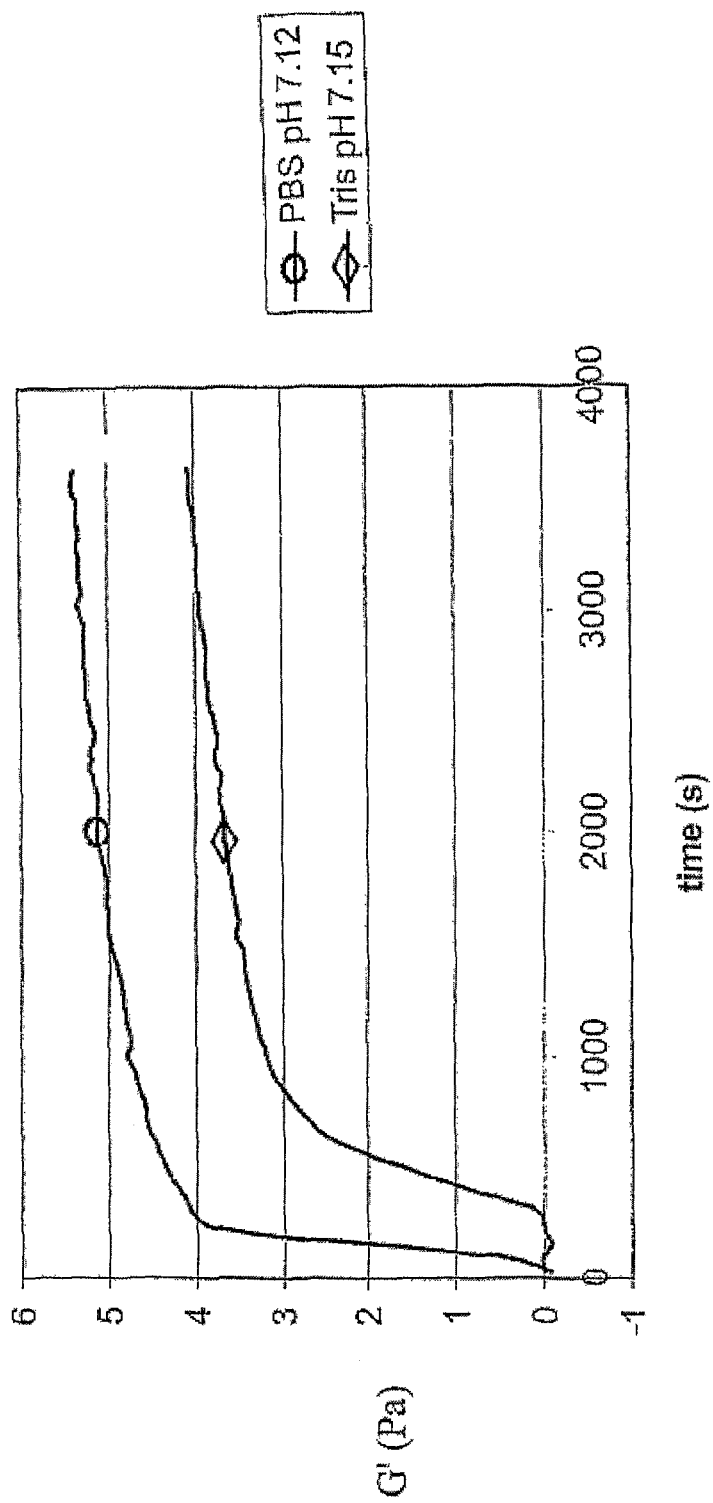
Figure 1C:
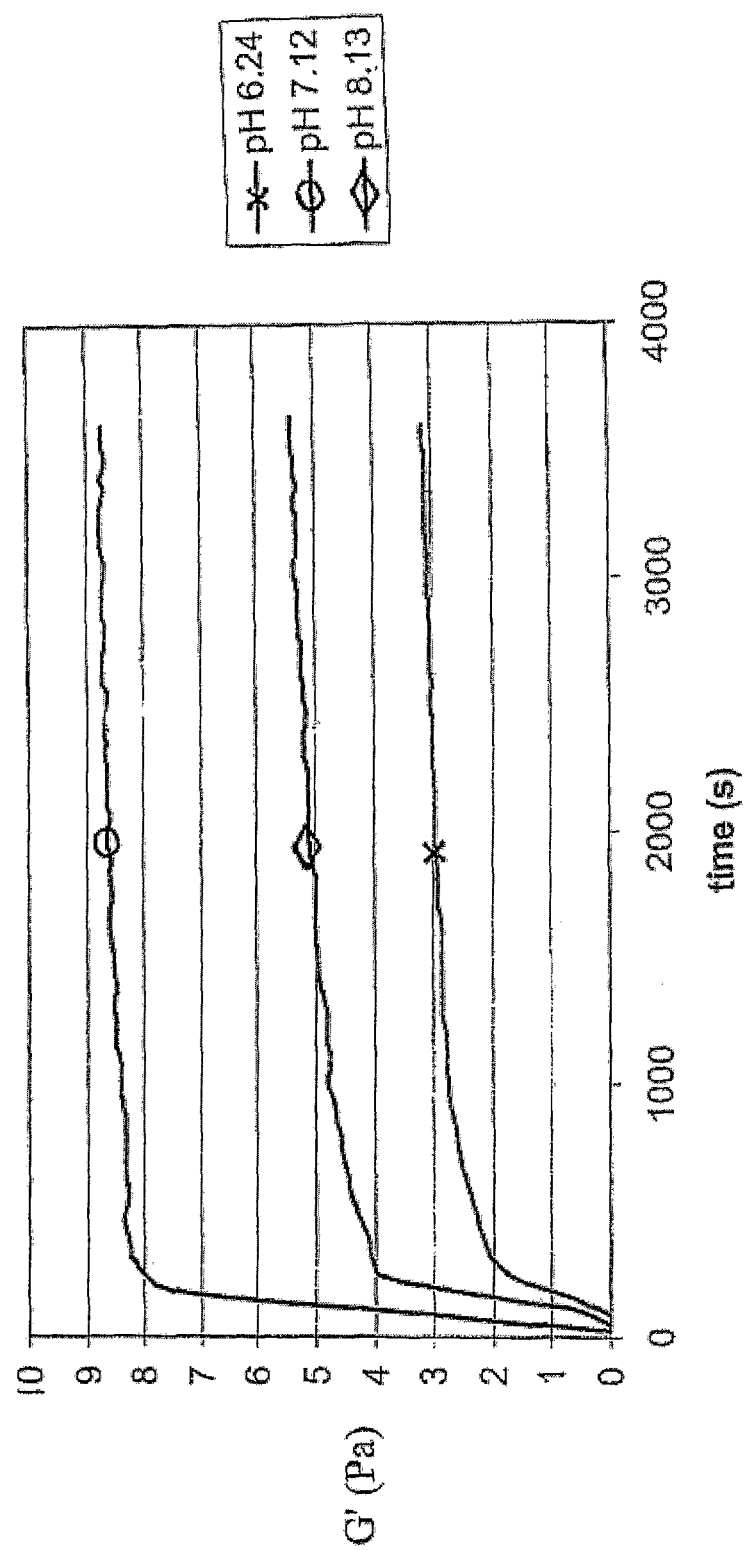
Figure 1D:
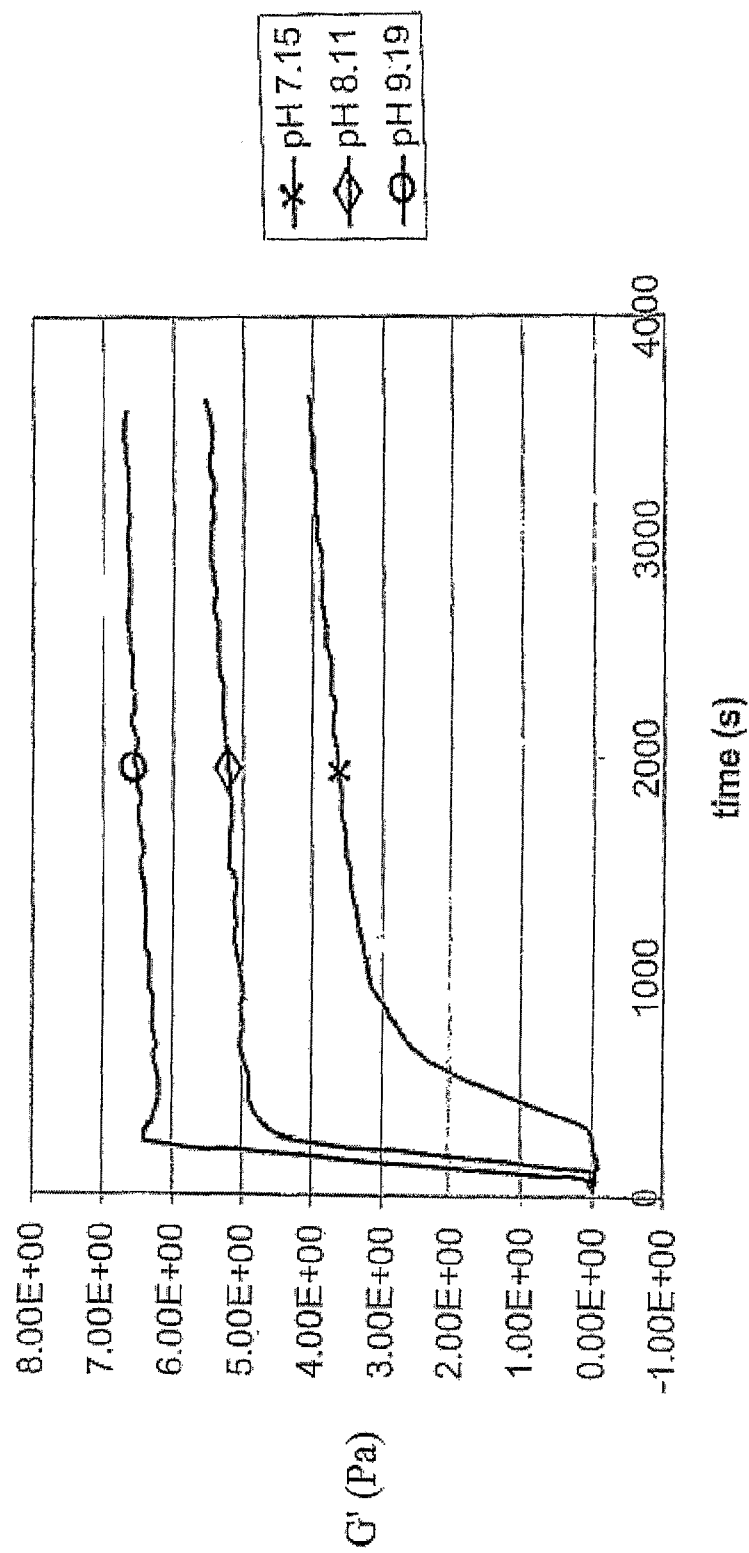
Figure 1E:
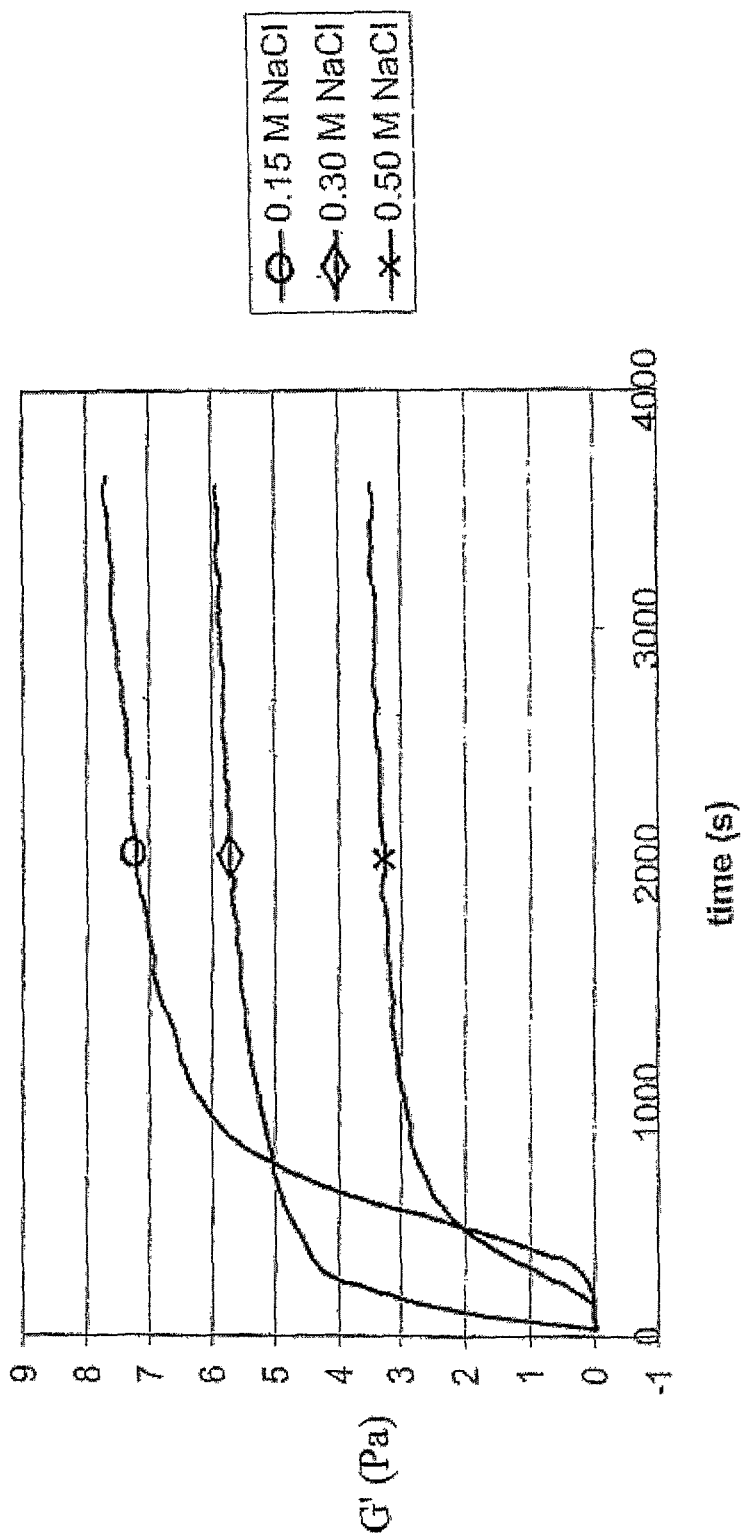
Figure 1F:
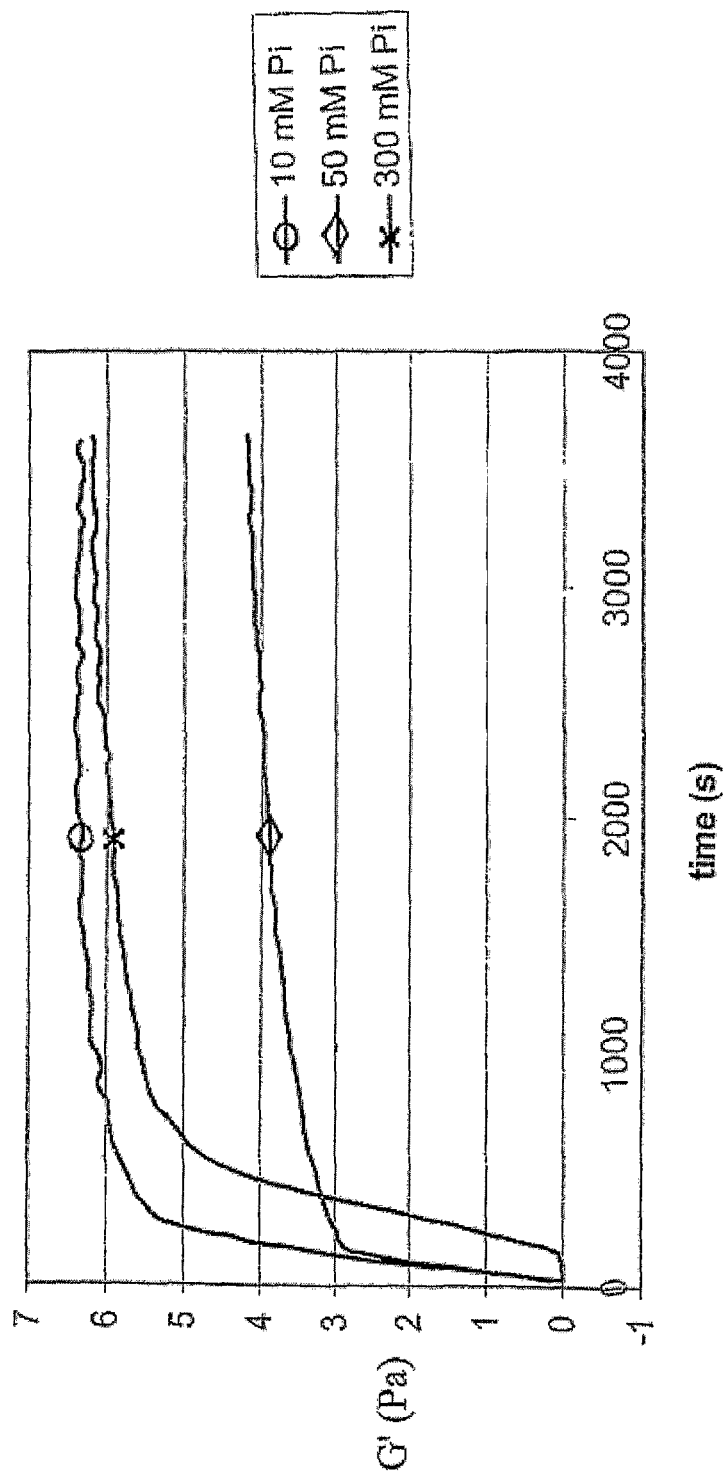
Figure 1G:
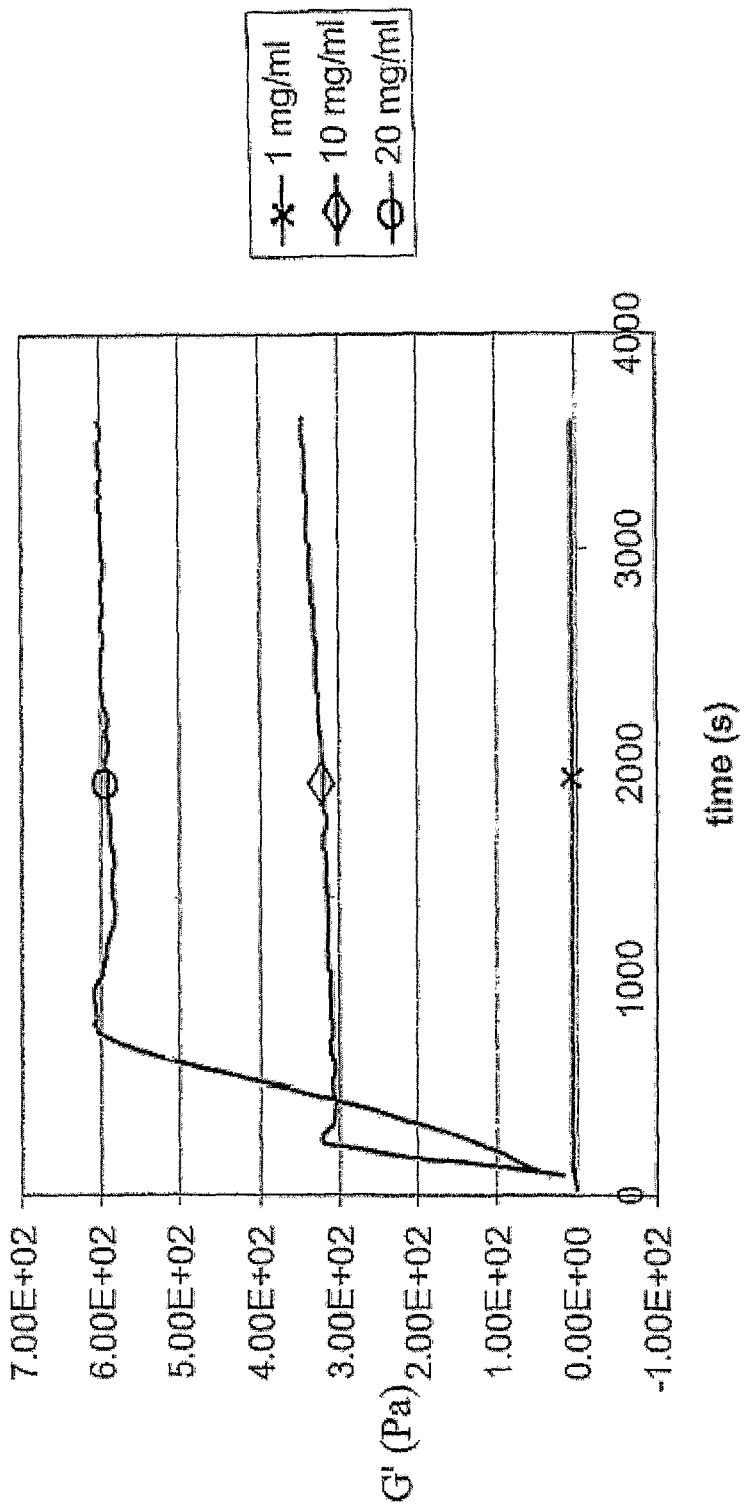
FIG. 1G shows the effect of solubilized extracellular matrix component concentration on a matrix formed from solubilized extracellular matrix components from submucosa tissue (SIS) in 1×PBS at 37° C.
Figure 2:
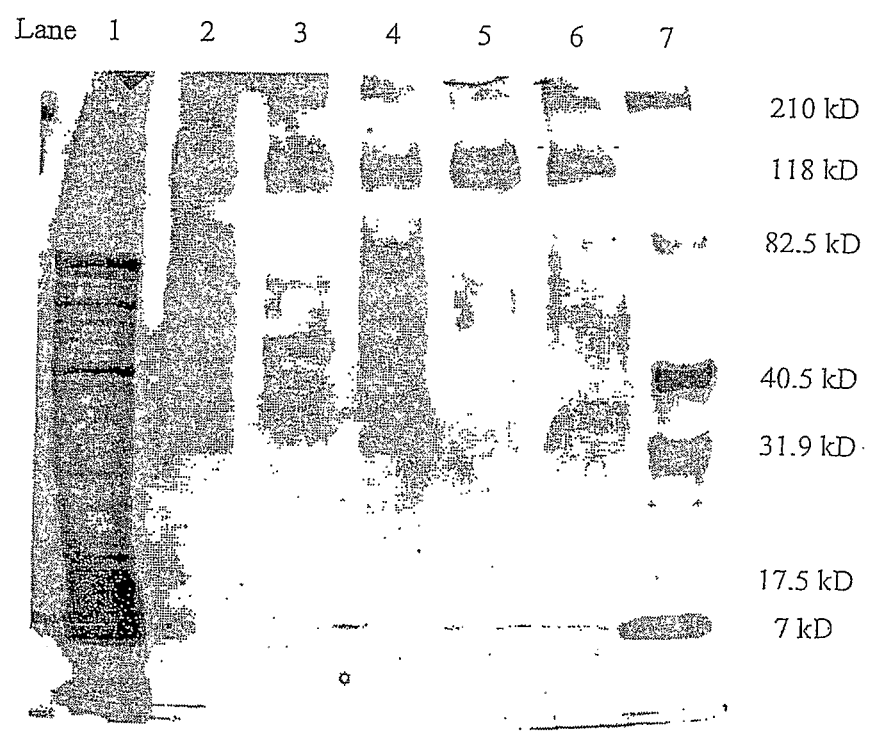
FIG. 2 shows an SDS-PAGE gel (4-20%) analysis of the protein composition of various small intestinal submucosa formulations. The preparations were acid solubilized small intestinal submucosa gel formulation (lane 1), pepsin/acid solubilized small intestinal submucosa tissue gel formulation (lane 2), pepsin/HCl solubilized small intestinal submucosa tissue (lane 3), pepsin/acetic acid solubilized small intestinal submucosa tissue (lane 4), Vitrogen collagen (lane 5) or Sigma Type I collagen (lane 6). All samples were dissolved at a concentration of 4 mg/ml. Lane 7 shows molecular weight standards.

As used herein, the term "lyophilized" means that water is removed from the composition, typically by freeze-drying under a vacuum. However, lyophilization can be performed by any method known to the skilled artisan and the method is not limited to freeze-drying under a vacuum.

As used herein "collagen-based matrix" means a matrix that comprises collagen. In illustrative embodiments, the "collagen-based matrices" described herein can be engineered from purified collagen ("engineered purified collagen-based matrix") or can be engineered from solubilized extracellular matrix components ("engineered ECM-based matrix").

As used herein "extracellular matrix material" or "extracellular matrix composition" means a material or composition derived from natural or native extracellular matrix tissue or a delaminated tissue thereof.

As used herein "solubilized extracellular matrix composition" refers to a composition derived from an extracellular matrix material that has been treated, for example, with an acid to reduce the molecular weight of at least some of the components of the extracellular matrix material and to produce a composition wherein at least some of the components of the extracellular matrix material have been solubilized from the extracellular matrix material. The "solubilized extracellular matrix composition" may include insoluble components of the extracellular matrix material as well as solubilized components.

As used herein "solubilized extracellular matrix components" means the extracellular matrix-derived components of a "solubilized extracellular matrix composition."

As used herein "engineered matrix" means a collagen-based matrix that is polymerized under conditions that are systematically varied where the conditions are selected from the group consisting of, but not limited to, pH, phosphate concentration, temperature, buffer composition, ionic strength, and composition and concentration of the solubilized extracellular matrix components. "Engineered matrices" include "engineered purified collagen-based matrices" and "engineered ECM-based matrices."

As used herein "sterilization" or "sterilize" or "sterilized" means removing unwanted contaminants including, but not limited to, endotoxins, nucleic acid contaminants, and infectious agents.

A lyophilized composition that maintains its biological properties (i.e., the capacity to form fibrils in vitro and in vivo and to remodel tissue in vivo) derived from components of solubilized extracellular matrix tissue of a warm-blooded vertebrate for use in making an engineered ECM-based matrix for specific tissue graft applications, has been difficult to obtain. Such a composition is useful commercially for the mass production of solubilized extracellular matrix components for use in making engineered ECM-based matrices for specific tissue graft applications. Lyophilized, solubilized extracellular matrix components would also allow for solubilized extracellular matrix components to be concentrated and then used for making engineered ECM-based matrices for specific tissue graft applications.

The present invention relates to a method of preparing a collagen-based matrix. In one illustrative embodiment, the method comprises the steps of solubilizing an extracellular matrix material with an acid, such as hydrochloric acid, formic acid, lactic acid, citric acid, sulfuric acid, ethanoic acid, carbonic acid, nitric acid, or phosphoric acid to produce a solubilized extracellular matrix composition, and polymerizing the solubilized extracellular matrix components to form fibrils. The polymerizing step can be performed under conditions that are systematically varied where the conditions are selected from the group consisting of pH, phosphate concentration, temperature, buffer composition, ionic strength, the specific solubilized extracellular matrix components present, and the concentration of the solubilized extracellular matrix components present. In another illustrative aspect, the solubilized extracellular matrix composition or components can be lyophilized prior to polymerization. The solubilized extracellular matrix composition or components can be lyophilized in an acid, such as hydrochloric acid, formic acid, lactic acid, citric acid, sulfuric acid, ethanoic acid, carbonic acid, nitric acid, or phosphoric acid.

In another illustrative embodiment, the invention relates to a three-dimensional collagen-based matrix prepared using the methods described above. The collagen-based matrix contains fibrils with specific characteristics, including, but not limited to, a fibril area fraction (i.e., density) of about 7% to about 26%, about 20% to about 30%, about 20% to about 50%, about 20% to about 70%, and about 20% to about 100%, about 30% to about 50%, about 30% to about 70%, and about 30% to about 100% and/or an elastic or linear modulus (i.e., stiffness) of about 0.5 kPa to about 40 kPa, about 30 kPa to 100 kPa, about 30 kPa to about 1000 kPa, about 30 kPa to about 10000 kPa, about 30 kPa to about 70000 kPa, about 100 kPa to 1000 kPa, about 100 kPa to about 10000 kPa, and about 100 kPa to about 70000 kPa.

Exemplary of tissues useful as a source of extracellular matrix material for making the collagen-based matrices described herein are submucosa tissues or any other extracellular matrix-derived tissues of a warm-blooded vertebrate. Exemplary methods of preparing submucosa tissues are described in U.S. Pat. Nos. 4,902,508, 5,281,422, and 5,275,826, each incorporated herein by reference. Extracellular matrix material-derived tissues other than submucosa tissue may be used in accordance with the methods and compositions described herein. Methods of preparing other extracellular matrix material-derived tissues are known to those skilled in the art. For example, see U.S. Pat. Nos. 5,163,955 (pericardial tissue), 5,554,389 (urinary bladder submucosa tissue), 6,099,567 (stomach submucosa tissue), 6,576,265 (extracellular matrix tissues generally), 6,793,939 (liver basement membrane tissues), and U.S. patent application publication no. US-2005-0019419-A1 (liver basement membrane tissues), and international publication no. WO 01/45765 (extracellular matrix tissues generally), each incorporated herein by reference.

In one illustrative embodiment, the extracellular matrix material used to make the collagen-based matrix can be derived from a vertebrate submucosa tissue source. Vertebrate submucosa tissue can be obtained from various sources, including intestinal tissue harvested from animals raised for meat production, including, for example, pigs, cattle and sheep or other warm-blooded vertebrates. Submucosa tissue can comprise submucosa tissue selected from the group consisting of intestinal submucosa, stomach submucosa, urinary bladder submucosa, uterine submucosa, and any other submucosa tissue that can be used to remodel endogenous tissue.

The submucosa tissue can comprise any delamination embodiment, including the tunica submucosa delaminated from both the tunica muscularis and at least the luminal portion of the tunica mucosa of a warm-blooded vertebrate. Such compositions can be prepared by mechanically removing the luminal portion of the tunica mucosa and the external muscle layers and/or lysing resident cells with hypotonic washes, such as water or saline under hypotonic conditions.

It is known that compositions comprising the tunica submucosa delaminated from both the tunica muscularis and at least the luminal portion of the tunica mucosa of the submucosal tissue of warm-blooded vertebrates can be used as tissue graft materials (see, for example, U.S. Pat. Nos. 4,902,508 and 5,281,422 incorporated herein by reference). Compositions comprising the tunica submucosa delaminated from both the tunica muscularis and at least the luminal portion of the tunica mucosa (i.e., the outer epithelial layers) of the submucosal tissue of warm-blooded vertebrates are also described in U.S. Pat. No. 5,554,389. Such submucosa tissue preparations are characterized by excellent mechanical properties, including high compliance, high tensile strength, a high burst pressure point, and tear-resistance.

Other advantages of submucosa tissue is its resistance to infection, stability, and lack of immunogenicity. Submucosa tissues, described in the aforesaid patents, have high infection resistance. Furthermore, this tissue is not recognized by the host's immune system as "foreign" and is not rejected. It has been found that xenogeneic intestinal submucosa tissue is not rejected following implantation as vascular grafts, ligaments, and tendons because of its composition (i.e., the extracellular matrix components of tissues are apparently similar among species).

Submucosa-derived matrices can be prepared as collagen based biodegradable matrices comprising highly conserved collagens, glycoproteins, proteoglycans, and glycosaminoglycans in their natural configuration and natural concentration. Such submucosa tissue can serve as a matrix for the regrowth of endogenous tissues at the implantation site (e.g., biological remodeling). The submucosa tissue can serve as a rapidly vascularized matrix for support and growth of new endogenous connective tissue. Thus, submucosa tissue can be prepared to be trophic for host tissues with which it is attached or otherwise associated in its implanted environment. In multiple experiments submucosa tissue has been found to be remodeled (resorbed and replaced with autogenous differentiated tissue) to assume the characterizing features of the tissue(s) with which it is associated at the site of implantation or insertion.

Small intestinal submucosa tissue is an illustrative source of submucosa tissue. Submucosa tissue can be obtained from various sources, for example, intestinal tissue can be harvested from animals raised for meat production, including, pigs, cattle and sheep or other warm-blooded vertebrates. Small intestinal submucosa tissue is a plentiful by-product of commercial meat production operations and is, thus, a low cost material.

Suitable intestinal submucosa tissue typically comprises the tunica submucosa delaminated from both the tunica muscularis and at least the luminal portion of the tunica mucosa, but other tissue constructs can also be used. In one illustrative embodiment, an intestinal-derived tissue comprises the tunica submucosa and basilar portions of the tunica mucosa including the lamina muscularis mucosa and the stratum compactum which layers are known to vary in thickness and in definition dependent on the source vertebrate species.

An illustrative preparation method for submucosa tissue is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells. The submucosa tissue is rinsed under hypotonic conditions, such as with water or with saline under hypotonic conditions and is optionally sterilized. The submucosa tissue can be stored in a hydrated or dehydrated state prior to solubilization.

In various illustrative embodiments, the submucosa tissue can be sterilized using conventional sterilization techniques including glutaraldehyde tanning, formaldehyde tanning at acidic pH, propylene oxide or ethylene oxide treatment, gas plasma sterilization, gamma radiation, electron beam, and/or peracetic acid sterilization. Sterilization techniques which do not adversely affect the structure and biotropic properties of the submucosal tissue can be used. An illustrative sterilization technique is exposing the submucosal tissue to peracetic acid, 1-4 Mrads gamma irradiation (or 1-2.5 Mrads of gamma irradiation), ethylene oxide treatment, or gas plasma sterilization. The submucosal tissue can be subjected to one or more sterilization processes. In an illustrative embodiment, the intact extracellular matrix source material can be sterilized, for example with peracetic acid.

In one illustrative embodiment, the extracellular matrix material is solubilized with an acid after it is obtained and prepared. Typically, prior to solubilization, the source extracellular matrix material is comminuted by tearing, cutting, grinding, or shearing the harvested extracellular matrix material. In one illustrative embodiment, the extracellular matrix material can be comminuted by shearing in a high-speed blender, or by grinding the extracellular matrix material in a frozen or freeze-dried state, and then lyophilizing the material to produce a powder having particles ranging in size from about 0.1 $mm^2$ to about 1.0 $mm^2$. The extracellular matrix material powder can thereafter be hydrated with, for example, water or buffered saline. In one illustrative embodiment, the extracellular matrix material is comminuted by freezing and pulverizing under liquid nitrogen in an industrial blender. The preparation of fluidized compositions from the source extracellular matrix material, such as submucosa tissue, is described in U.S. Pat. Nos. 5,275,826 and 6,444,229, the disclosures of which are expressly incorporated herein by reference.

In one illustrative embodiment, an acid, such as hydrochloric acid, formic acid, lactic acid, citric acid, sulfuric acid, ethanoic acid, carbonic acid, nitric acid, or phosphoric acid, is used to solubilize the source extracellular matrix material. In various illustrative embodiments, the acidic conditions for solubilization can include solubilization at about 0° C. to about 60° C., and incubation periods of about 5 minutes to about 96 hours. In other illustrative embodiments, the concentration of the acid, such as hydrochloric acid, can be from about 0.001 N to about 0.1 N, from about 0.005 N to about 0.1 N, from about 0.01 N to about 0.1 N, from about 0.05 N to about 0.1 N, from about 0.001 N to about 0.05 N, about 0.001 N to about 0.01 N, or from about 0.01 N to about 0.05 N. In one illustrative embodiment, the extracellular matrix material can be solubilized with 0.01 N HCl. However, the solubilization can be conducted at any temperature, for any length of time, and at any concentration of acid.

Any of the source extracellular matrix materials described above can be used and the solubilization step can be performed in the presence of an acid or in the presence of an acid and an enzyme. The acid solubilization step results in a solubilized extracellular matrix composition that includes collagen that remains bioactive (i.e., is capable of polymerizing into fibrils in vitro and in vivo and remodeling tissues in vivo) after lyophilization.

In one illustrative embodiment, the extracellular matrix material is treated with one or more enzymes before, during, or after the acid solubilization step. For enzymes that are inactive at acidic pH, for example, the extracellular matrix material is treated with the enzyme before the acid solubilization step or after the acid solubilization step, but under conditions that are not acidic. Enzymatic digestion of the extracellular matrix material is conducted under conditions that are optimal for the specific enzyme used and under conditions that retain the ability of the solubilized components of the extracellular matrix material to polymerize (i.e., to form fibrils). The concentration of the enzyme depends on the specific enzyme used, the amount of extracellular matrix material to be digested, the desired time of digestion, and the desired temperature of the reaction. In various illustrative embodiments, about 0.01% to about 0.5% weight/volume of enzyme is used. Exemplary enzymes include pepsin, bromelain, cathepsins, chymotrypsin, elastase, papain, pepsin, plasmin, subtilisin, thrombin, trypsin, matrix metalloproteinases (e.g., stromelysin and elastase), glycosaminoglycan-specific enzymes (e.g., chondroitinase, hyaluronidase, and heparinase), and the like, or combinations thereof. The source extracellular matrix material can be treated with one or more enzymes. In illustrative embodiments, the enzyme digestion can be performed at about 0° C. to about 60° C. However, the digestion can be conducted at any temperature, for any length of time (e.g., about 5 minutes to about 96 hours), and at any enzyme concentration.

In illustrative embodiments, the ratio of the extracellular matrix material (hydrated) to total enzyme (weight/weight) ranges from about 25 to about 2500. In one illustrative embodiment where an enzyme is used, it can be removed (e.g., by fractionation) or inactivated after the desired incubation period for the digestion so as to not compromise stability of the solubilized extracellular matrix components. Enzymes, such as pepsin for example, can be inactivated with protease inhibitors, a shift to neutral pH, a drop in temperature below 0° C., or heat inactivation, or a combination of these methods. The enzyme can be removed or inactivated at any step in the methods described herein.

In another illustrative embodiment, the source extracellular matrix material can be extracted in addition to being solubilized with an acid and/or treated with an enzyme. Extraction methods for extracellular matrices are known to those skilled in the art and are described in detail in U.S. Pat. No. 6,375,989, incorporated herein by reference. Illustrative extraction excipients include, for example, chaotropic agents such as urea, guanidine, sodium chloride or other neutral salt solutions, magnesium chloride, and non-ionic or ionic surfactants.

In one illustrative aspect, the solubilized extracellular matrix composition (i.e., extracellular matrix material treated with an enzyme, an acid, or an extraction excipient, or a combination thereof) comprises soluble and insoluble components and at least a portion of the insoluble components of the solubilized extracellular matrix composition can be separated from the soluble components. For example, the insoluble components can be separated from the soluble components by centrifugation (e.g., at 12,000 rpm for 20 minutes at 4° C.). In alternative embodiments, other separation techniques known to those skilled in the art, such as filtration, can be used.

In accordance with one illustrative embodiment, the solubilized extracellular matrix composition, prepared with or without the above-described separation step, is fractionated prior to polymerization (i.e., fibril formation). In one illustrative aspect, the solubilized extracellular matrix composition can be fractionated by dialysis. Exemplary molecular weight cut-offs for the dialysis tubing or membrane are from about 3,500 to about 12,000 or about 3,500 to about 5,000. In one embodiment, the solubilized extracellular matrix composition is dialyzed against an acidic solution having a low ionic strength. For example, the solubilized extracellular matrix composition can be dialyzed against a hydrochloric acid solution, but any other acids including acetic acid, formic acid, lactic acid, citric acid, sulfuric acid, ethanoic acid, carbonic acid, nitric acid, or phosphoric acid can be used.

In various illustrative embodiments, the fractionation, for example by dialysis, can be performed at about 2° C. to about 37° C. for about 1 hour to about 96 hours. In another illustrative embodiment, and the concentration of the acid, such as acetic acid, hydrochloric acid, formic acid, lactic acid, citric acid, sulfuric acid, ethanoic acid, carbonic acid, nitric acid, or phosphoric acid, against which the solubilized extracellular matrix composition is dialyzed can be from about 0.001 N to about 0.1 N, from about 0.005 N to about 0.1 N, from about 0.01 N to about 0.1 N, from about 0.05 N to about 0.1 N, from about 0.001 N to about 0.05 N, about 0.001 N to about 0.01 N, or from about 0.01 N to about 0.05 N. In one illustrative embodiment, the solubilized extracellular matrix composition can be dialyzed against 0.01 N HCl. However, the fractionation can be performed at any temperature, for any length of time, and against any concentration of acid.

As discussed above, the term "lyophilized" means that water is removed from the composition, typically by freeze-drying under a vacuum. In one illustrative aspect, the solubilized extracellular matrix composition is lyophilized after solubilization. In another illustrative aspect, the solubilized extracellular matrix composition is lyophilized after the separation step used to separate soluble from insoluble extracellular matrix components. In yet another illustrative aspect, the solubilized extracellular matrix composition is lyophilized after the fractionation step. In another illustrative embodiment, the polymerized matrix itself is lyophilized. In one illustrative lyophilization embodiment, the solubilized extracellular matrix composition is first frozen, and then placed under a vacuum. In another lyophilization embodiment, the solubilized extracellular matrix composition is freeze-dried under a vacuum. Any method of lyophilization known to the skilled artisan can be used.

In accordance with one illustrative embodiment, the solubilized extracellular matrix composition is sterilized. Exemplary sterilizing agents are described above, but any sterilizing agent or method of sterilization known in the art can be used. The solubilized extracellular matrix composition can be sterilized using glutaraldehyde, formaldehyde, acidic pH, propylene oxide, ethylene oxide, gas plasma sterilization, gamma radiation, electron beam sterilization, or peracetic acid sterilization, or combinations thereof, and the like. Sterilization techniques which do not adversely affect the structure and biotropic properties of the components of the solubilized extracellular matrix composition can be used. Illustrative sterilization techniques are exposing the solubilized extracellular matrix composition to peracetic acid, 1-4 Mrads gamma irradiation (or 1-2.5 Mrads of gamma irradiation), ethylene oxide treatment, or gas plasma sterilization.

The solubilized extracellular matrix composition can be sterilized before the separation step and before lyophilization if those steps are included. In another illustrative embodiment the source extracellular matrix material used for solubilization is sterilized. Sterilization of the source extracellular matrix material can be performed, for example, as described in U.S. Pat. Nos. 4,902,508 and 6,206,931, incorporated herein by reference. In yet another embodiment, the solubilized extracellular matrix composition is sterilized after the separation step, but before lyophilization if those steps are included. In still other embodiments, the solubilized extracellular matrix composition is sterilized after the fractionation step, but before lyophilization or the solubilized extracellular matrix composition is sterilized after the lyophilized composition is redissolved or rehydrated if each of those steps is included. In another illustrative embodiment, the lyophilized composition itself is sterilized before rehydration, for example using an e-beam sterilization technique. In yet another illustrative embodiment, the polymerized matrix formed from the solubilized extracellular matrix components is sterilized.

In one illustrative embodiment, the solubilized extracellular matrix composition is directly sterilized before the separation step, for example, with peracetic acid or with peracetic acid and ethanol (e.g., by the addition of 0.18% peracetic acid and 4.8% ethanol to the solubilized extracellular matrix composition before the separation step). In another embodiment, sterilization can be carried out during the fractionation step.

For example, the solubilized extracellular matrix composition can be dialyzed against chloroform, peracetic acid, or a solution of peracetic acid and ethanol to disinfect or sterilize the solubilized extracellular matrix composition. Illustratively, the solubilized extracellular matrix composition can be sterilized by dialysis against a solution of peracetic acid and ethanol (e.g., 0.18% peracetic acid and 4.8% ethanol). The chloroform, peracetic acid, or peracetic acid/ethanol can be removed prior to lyophilization, for example by dialysis against an acid, such as 0.01 N HCl. In an alternative embodiment, the lyophilized composition can be sterilized directly after rehydration, for example, by the addition of 0.18% peracetic acid and 4.8% ethanol. In this embodiment, the sterilizing agent can be removed prior to polymerization of the solubilized extracellular matrix components to form fibrils.

If the solubilized extracellular matrix composition is lyophilized, the lyophilized composition can be stored frozen or at room temperature (for example, at about −80° C. to about 25° C.). Storage temperatures are selected to stabilize the solubilized extracellular matrix components. The compositions can be stored for about 1-26 weeks, or longer. In one illustrative embodiment, the lyophilizate is stored in a hydrochloric acid solution. For example, hydrochloric acid, or other acids, at concentrations of from about 0.001 N to about 0.1 N, from about 0.005 N to about 0.1 N, from about 0.01 N to about 0.1 N, from about 0.05 N to about 0.1 N, from about 0.001 N to about 0.05 N, from about 0.001 N to about 0.01 N, or from about 0.01 N to about 0.05 N can be used for storage of the lyophilized, solubilized extracellular matrix components. Other acids can be used as adjuvants for storage including acetic acid, formic acid, lactic acid, citric acid, sulfuric acid, ethanoic acid, carbonic acid, nitric acid, or phosphoric acid, and these acids can be used at any of the above-described concentrations. In one illustrative embodiment, the lyophilizate can be stored (e.g., lyophilized in and stored in) an acid, such as acetic acid, at a concentration of from about 0.001 N to about 0.5 N or from about 0.01 N to about 0.5 N. In another embodiment, the lyophilizate can be stored in water with a pH of about 6 or below. In other illustrative embodiments, lyoprotectants, cryoprotectants, lyophilization accelerators, or crystallizing excipients (e.g., ethanol, isopropanol, mannitol, trehalose, maltose, sucrose, tert-butanol, and tween 20), or combinations thereof, and the like can be present during lyophilization.

In one embodiment, the sterilized, solubilized extracellular matrix composition can be dialyzed against 0.01 N HCl, for example, prior to lyophilization to remove the sterilization solution and so that the solubilized extracellular matrix components are in a 0.01 N HCl solution. Alternatively, the solubilized extracellular matrix composition can be dialyzed against acetic acid, for example, prior to lyophilization and can be lyophilized in acetic acid and redissolved in HCl or water.

If the solubilized extracellular matrix composition is lyophilized, the resulting lyophilizate can be redissolved in any solution, but may be redissolved in an acidic solution or water. The lyophilizate can be redissolved in, for example, acetic acid, hydrochloric acid, formic acid, lactic acid, citric acid, sulfuric acid, ethanoic acid, carbonic acid, nitric acid, or phosphoric acid, at any of the above-described concentrations, or can be redissolved in water. In one illustrative embodiment the lyophilizate is redissolved in 0.01 N HCl. For use in producing engineered ECM-based matrices that can be injected in vivo or used for other purposes in vitro, the redissolved lyophilizate can be subjected to varying conditions (e.g., pH, phosphate concentration, temperature, buffer composition, ionic strength, and composition and concentration of solubilized extracellular matrix components (dry weight/ml)) that result in polymerization to form engineered ECM-based matrices for specific tissue graft applications.

For use in producing engineered ECM-based matrices that can be 1.) injected in vivo and used for specific tissue graft applications or 2.) used for other purposes in vitro, such as studying cell-extracellular matrix interactions, the solubilized extracellular matrix components can be subjected to varying conditions for polymerization to form fibrils. In illustrative embodiments, the conditions that can be varied include pH, phosphate concentration, temperature, buffer composition, ionic strength, the particular solubilized extracellular matrix components in the solubilized extracellular matrix composition, and the concentration of solubilized extracellular matrix components (dry weight/ml). These conditions result in polymerization of the solubilized extracellular matrix components to form engineered ECM-based matrices with desired compositional, microstructural, and mechanical characteristics. Illustratively, these compositional, microstructural, and mechanical characteristics can include fibril length, fibril diameter, number of fibril-fibril connections, fibril density, fibril organization, matrix composition, 3-dimensional shape or form, viscoelastic, tensile, or compressive behavior, shear (e.g., failure stress, strain, and moduli), permeability, swelling, hydration properties (e.g., rate and swelling), and in vivo tissue remodeling and bulking properties, and desired in vitro cell responses. The collagen-based matrices described herein have desirable biocompatibility, vascularization, remodeling, and bulking properties, among other desirable properties.

In various illustrative embodiments, qualitative and quantitative microstructural characteristics of the engineered matrices can be determined by environmental or cryostage scanning electron microscopy, transmission electron microscopy, confocal microscopy, second harmonic generation multi-photon microscopy. In another embodiment, polymerization kinetics may be determined by spectrophotometry or time-lapse confocal reflection microscopy. In another embodiment, tensile, compressive and viscoelastic properties can be determined by rheometry or uniaxial tensile testing. In another embodiment, a rat subcutaneous injection model can be used to determine remodeling and bulking properties. All of these methods are known in the art or are further described in Examples 5-7 or are described in Roeder et al., *J. Biomech. Eng.*, vol. 124, pp. 214-222 (2002), in Pizzo et al., *J. Appl. Physiol.*, vol. 98, pp. 1-13 (2004), Fulzele et al., *Eur. J. Pharm. Sci.*, vol. 20, pp. 53-61 (2003), Griffey et al., *J. Biomed. Mater. Res.*, vol. 58, pp. 10-15 (2001), Hunt et al., *Am. J. Surg.*, vol. 114, pp. 302-307 (1967), and Schilling et al., *Surgery*, vol. 46, pp. 702-710 (1959), incorporated herein by reference.

In accordance with one embodiment, the solubilized extracellular matrix components are polymerized to form fibrils at a final concentration (dry weight/ml) of about 0.25 to about 5.0 mg/ml of the solubilized components, or in another embodiment the final concentration is selected from the range of about 0.5 mg/ml to about 4.0 mg/ml, and in another embodiment the final concentration is selected from the range of about 1.0 mg/ml to about 3.0 mg/ml, and in another embodiment the final concentration is about 0.3, 0.5, 1.0, 2.0, or 3.0 mg/ml. In other embodiments, the solubilized extracellular matrix components are polymerized at final concentrations (dry weight/ml) of about 5 to about 10 mg/ml, about 5 to about 30 mg/ml, about 5 to about 50 mg/ml, about 5 to about 100 mg/ml, about 20 to about 50 mg/ml, about 20 to about 60 mg/ml, or about 20 to about 100 mg/ml.

In various illustrative embodiments, the polymerization reaction is conducted in a buffered solution using any biologically compatible buffer known to those skilled in the art. For example, the buffer may be selected from the group consisting of phosphate buffer saline (PBS), Tris (hydroxymethyl) aminomethane Hydrochloride (Tris-HCl), 3-(N-Morpholino) Propanesulfonic Acid (MOPS), piperazine-n,n'-bis (2-ethanesulfonic acid) (PIPES), [n-(2-Acetamido)]-2-Aminoethanesulfonic Acid (ACES), N-[2-hydroxyethyl] piperazine-N'-[2-ethanesulfonic acid] (HEPES), and 1,3-bis [tris(Hydroxymethyl)methylamino]propane (Bis Tris Propane). In one embodiment the buffer is PBS, Tris, or MOPS and in one embodiment the buffer system is PBS.

In various illustrative embodiments, the polymerization of the solubilized extracellular matrix components is conducted at a pH selected from the range of about 5.0 to about 11, and in one embodiment polymerization is conducted at a pH selected from the range of about 6.0 to about 9.0, and in one embodiment polymerization is conducted at a pH selected from the range of about 6.5 to about 8.5, and in another embodiment the polymerization of the solubilized extracellular matrix components is conducted at a pH selected from the range of about 7.0 to about 8.5, and in another embodiment the polymerization of the solubilized extracellular matrix components is conducted at a pH selected from the range of about 7.3 to about 7.4.

In other illustrative aspects, the ionic strength of the buffered solution is also regulated. In accordance with one embodiment, the ionic strength of the buffer used to polymerize the solubilized extracellular matrix components is selected from a range of about 0.05 to about 1.5 M, in another embodiment the ionic strength is selected from a range of about 0.10 to about 0.90 M, in another embodiment the ionic strength is selected from a range of about 0.14 to about 0.30 M and in another embodiment the ionic strength is selected from a range of about 0.14 to about 0.17 M.

In still other illustrative embodiments, the polymerization is conducted at temperatures selected from the range of about 0° C. to about 60° C. In other embodiments, the polymerization is conducted at temperatures above 20° C., and typically the polymerization is conducted at a temperature selected from the range of about 20° C. to about 40° C., and more typically the temperature is selected from the range of about 30° C. to about 40° C. In one illustrative embodiment the polymerization is conducted at about 37° C.

In yet other embodiments, the phosphate concentration is varied. For example, in one embodiment, the phosphate concentration is selected from a range of about 0.005 M to about 0.5 M. In another illustrative embodiment, the phosphate concentration is selected from a range of about 0.01 M to about 0.2 M. In another embodiment, the phosphate concentration is selected from a range of about 0.01 M to about 0.1 M. In another illustrative embodiment, the phosphate concentration is selected from a range of about 0.01 M to about 0.03 M.

In other illustrative embodiments, the solubilized extracellular matrix components can be polymerized by, for example, dialysis against a solution under any of the above-described conditions (e.g., dialysis against PBS at pH 7.4), extrusion or co-extrusion of polymerized submucosa formulations into a desired buffer, including the buffers described above, or wet-spinning to form strands of extracellular matrix material.

In one embodiment the strands can be formed by extrusion through a needle and can be air-dried to form fibers or threads of various dimensions. The syringe can be adapted with needles or tubing to control the dimensions (e.g., diameter) of the fibers or threads. In one embodiment, the extrusion process involves polymerization of the solubilized extracellular matrix components followed by extrusion into a bath containing water, a buffer, or an organic solvent (e.g., ethanol). In another embodiment, the extrusion process involves coextrusion of the solubilized extracellular matrix components with a polymerization buffer (e.g., the buffer such as Tris or phosphate buffers at various concentrations can be varied to control pH and ionic strength). In yet another embodiment, the extrusion process involves extrusion of the solubilized extracellular matrix components into a polymerization bath (e.g., the buffer such as Tris or phosphate buffers at various concentrations can be varied to control pH and ionic strength). The bath conditions affect polymerization time and properties of the fibers or threads, such as mechanical integrity of the fibers or threads, fiber dimensions, and the like. In one embodiment, the fibers can be air-dried to create materials suitable for use as sutures.

In various illustrative embodiments, the engineered ECM-based matrices can be polymerized from the solubilized extracellular matrix composition at any step in the above-described methods. For example, the engineered ECM-based matrices can be polymerized from the solubilized extracellular matrix composition after the solubilization step or after the separation step, the filtration step, or the lyophilization and rehydration steps, if the separation step, the filtration step, and/or the lyophilization and rehydration steps are performed.

The engineered ECM-based matrices of the present invention can be combined, prior to, during, or after polymerization, with nutrients, including minerals, amino acids, sugars, peptides, proteins, vitamins (such as ascorbic acid), or glycoproteins that facilitate cellular proliferation, such as laminin and fibronectin, hyaluronic acid, or growth factors such as epidermal growth factor, platelet-derived growth factor, transforming growth factor beta, or fibroblast growth factor, and glucocorticoids such as dexamethasone. In other illustrative embodiments, fibrillogenesis inhibitors, such as glycerol, glucose, or polyhydroxylated compounds can be added prior to or during polymerization. In accordance with one embodiment, cells can be added to the solubilized extracellular matrix components as the last step prior to the polymerization or after polymerization of the engineered ECM-based matrix. In another illustrative embodiment, particulate extracellular matrix materials can be added to the solubilized extracellular matrix components and can enhance bulking capacity. In other illustrative embodiments, cross-linking agents, such as carbodiimides, aldehydes, lysl-oxidase, N-hydroxysuccinimide esters, imidoesters, hydrazides, and maleimides, and the like can be added before, during, or after polymerization.

Accordingly, in one illustrative embodiment, a lyophilized, solubilized extracellular matrix composition is prepared by enzymatically treating the source extracellular matrix material with 0.1% (w/v) pepsin in 0.01 N HCl to produce a solubilized extracellular matrix composition, centrifuging the solubilized composition at 12,000 rpm for 20 minutes at 4° C. to remove insoluble components, fractionating the soluble fraction (i.e., the supernatant) by dialysis against a 0.01 N HCl solution, and then lyophilizing the dialyzed fraction. The lyophilized composition is then redissolved in 0.01 N HCl and the solubilized extracellular matrix components are polymerized under any of the polymerization conditions described above.

In another illustrative embodiment, a fractionation step is not performed. In this embodiment, the source extracellular matrix material is enzymatically treated with 0.1% (w/v) pepsin in a 0.01 N hydrochloric acid solution to produce a solubilized extracellular matrix composition, the solubilized extracellular matrix composition is centrifuged at 12,000 rpm for 20 minutes at 4° C. to remove insoluble components, and then the solubilized fraction (i.e., the supernatant) is lyophilized. The lyophilized composition is then redissolved in 0.01 N HCl and the solubilized extracellular matrix components are polymerized under any of the polymerization conditions described above.

In another illustrative embodiment, a lyophilized solubilized extracellular matrix composition is prepared by grinding source vertebrate submucosa tissue into a powder and enzymatically digesting the powderized submucosa tissue with 0.1% pepsin (w/v) and solubilizing in 0.01 N HCl for one to three days at 4° C. Following digestion and solubilization, the solubilized extracellular matrix components are separated from the insoluble components by centrifugation at 12,000 rpm at 4° C. for 20 minutes. The supernatant, comprising the soluble components, is recovered and the pellet containing insoluble components is discarded. The supernatant is then fractionated by dialyzing the solubilized extracellular matrix composition against 0.01 N HCl. In one embodiment, the solubilized extracellular matrix composition is dialyzed against several changes of 0.01 N hydrochloric acid at 4° C. using dialysis membranes having a molecular weight cut-off of 3500. Thus, the solubilized extracellular matrix composition is fractionated to remove components having a molecular weight of less than about 3500. Alternatively, dialysis tubing or membranes having a different molecular weight cut-off can be used. The fractionated solubilized extracellular matrix composition is then lyophilized and is stored in lyophilized form. The lyophilized composition is then redissolved in 0.01 N HCl and the solubilized extracellular matrix components are polymerized under any of the polymerization conditions described above.

In accordance with another illustrative embodiment, a lyophilized, solubilized extracellular matrix composition is prepared by grinding vertebrate submucosa into a powder and digesting the powderized submucosa composition with 0.1% pepsin (w/v) and solubilizing in 0.01M hydrochloric acid for one to three days at 4° C. Following digestion and solubilization, the solubilized extracellular matrix components are separated from the insoluble components by centrifugation at 12,000 rpm at 4° C. for 20 minutes. The supernatant, comprising the solubilized extracellular matrix components, is recovered and the pellet containing insoluble components is discarded. The non-fractionated solubilized extracellular matrix composition is then lyophilized and the resulting composition is stored in lyophilized form. The lyophilized composition is then redissolved in 0.01 N HCl and the solubilized extracellular matrix components are polymerized under any of the polymerization conditions described above.

In accordance with another illustrative embodiment, a solubilized extracellular matrix composition is prepared by enzymatically treating the source extracellular matrix material with 0.1% (w/v) pepsin in 0.01 N HCl to produce a solubilized extracellular matrix composition, centrifuging the solubilized extracellular matrix composition at 12,000 rpm for 20 minutes at 4° C. to remove insoluble components, and polymerizing the solubilized extracellular matrix components under any of the polymerization conditions described above.

In accordance with another illustrative embodiment, a solubilized extracellular matrix composition is prepared by grinding vertebrate submucosa into a powder and digesting the powderized submucosa composition with 0.1% pepsin (w/v) and solubilizing in 0.01 M hydrochloric acid for one to three days at 4° C. Following digestion and solubilization, the solubilized extracellular matrix components are separated from the insoluble components by centrifugation at 12,000 rpm at 4° C. for 20 minutes. The supernatant, comprising the solubilized extracellular matrix components, is recovered and the pellet containing insoluble components is discarded. The non-fractionated solubilized extracellular matrix composition is then polymerized under any of the polymerization conditions described above. In any of the above described embodiments, the enzyme digestion step can be eliminated and the solubilized extracellular matrix composition can be sterilized at any step in the method including following rehydration of the lyophilized composition.

The engineered ECM-based matrices are derived from extracellular matrix material comprising highly conserved collagens, glycoproteins, such as laminin and fibronectin, proteoglycans, such as serglycin, versican, decorin, and perlecan, and glycosaminoglycans in their natural configuration and natural concentration. The present invention enables the formation of a bioactive, solubilized extracellular matrix composition from a complex extracellular matrix material without purification of the matrix components. However, the components of the solubilized extracellular matrix composition described herein can be purified or partially purified and the purified or partially purified composition can be used in accordance with the methods described herein or mixtures of partially purified or purified components can be used. Purification methods for extracellular matrix components are known to those skilled in the art and are described in detail in U.S. Pat. No. 6,375,989, incorporated herein by reference.

Also provided are methods of making engineered matrices using collagen that is purified using partially purified commercially available material. For example, partially purified collagen is available from Sigma Chemical Co. (St. Louis, Mo.). Partially purified collagen can be obtained commercially and can be purified and polymerized under any of the conditions described above to produce an engineered purified collagen-based matrix having desired compositional, microstructural, and mechanical characteristics for specific tissue engineering devices or applications. As used herein, the term "purified" means the isolation of collagen in a form that is substantially free from other components (e.g., typically the total amount of other components present in the composition represents less than 5%, or more typically less than 0.1%, of total dry weight).

In one embodiment, an engineered purified collagen-based matrix is formed using commercially available collagen that has been purified by dialyzing against an acidic solution, including for example, hydrochloric acid. In another embodiment, the dialysis is performed against a 0.01 N HCl solution. In yet another embodiment, about 0.001 N to about 0.1 N HCl is used. In other illustrative embodiments, greater than 75% of the purified collagen or greater than 90% of the purified collagen is in monomeric form. The purified collagen is polymerized under any of the conditions described above to obtain an engineered purified collagen-based matrix.

In another illustrative aspect, an engineered purified collagen-based matrix is formed using commercially available collagen that has been purified by dialyzing against an aqueous solution. In another illustrative aspect, the purified collagen in an aqueous solution is dissolved in about 0.001 N to about 0.1 N, from about 0.005 N to about 0.1 N, from about 0.005 N to about 0.01 N, from about 0.01 N to about 0.1 N, from about 0.05 N to about 0.1 N, from about 0.001 N to about 0.05 N, about 0.001 N to about 0.01 N, or from about 0.01 N to about 0.05 N hydrochloric acid solution before polymerization to form the engineered purified collagen-based matrix. The purified collagen is polymerized under any of the conditions described above to obtain an engineered purified collagen-based matrix.

In any of the embodiments described above using purified collagen, the purified collagen can be sterilized after purification. In yet other embodiments, the purified collagen can be sterilized before or during the purification process. In other embodiments, the purified collagen can be sterilized before polymerization or the engineered purified collagen-based matrix can be sterilized after polymerization.

In additional illustrative embodiments, three-dimensional engineered purified collagen-based matrices and three-dimensional engineered ECM-based matrices are provided. The three-dimensional engineered matrices can be prepared according to any of the methods described herein, including any of the methods or conditions for polymerization described herein. The three-dimensional engineered matrices comprise collagen fibrils. As used herein the term "collagen fibril" refers to a quasi-crystalline, filamentous structure formed by the self-assembly of soluble trimeric collagen molecules. The three-dimensional engineered collagen matrices comprise collagen fibrils which typically pack in a quarter-staggered pattern giving the fibril a characteristic striated appearance or banding pattern along its axis. Collagen fibrils are distinct from the amorphous aggregates or precipitates of insoluble collagen that can be formed by dehydrating (e.g., lyophilizing) collagen suspensions to form porous network scaffolds.

Typically, the three-dimensional matrices are prepared from purified collagen or solubilized extracellular matrix components at collagen concentrations ranging from about 0.2 to about 5.0 mg/ml, about 1.0 mg/ml to about 3.0 mg/ml, about 0.2 mg/mil to about 10 mg/ml, about 0.2 to about 20 mg/ml, about 0.2 to about 30 mg/ml, about 0.2 to about 40 mg/ml, about 0.2 to about 50 mg/ml, about 0.2 to about 60 mg/ml, about 0.2 to about 80 mg/ml, about 5 mg/ml to 10 mg/ml, about 5 mg/ml to 20 mg/ml, about 5 mg/ml to about 40 mg/ml, about 5 mg/ml to 60 mg/ml, about 5 mg/ml to about 100 mg/ml, about 20 mg/ml to about 40 mg/ml, about 20 mg/ml to 60 mg/ml, or about 20 mg/ml to about 100 mg/ml. Table 1 summarizes the effect of total collagen concentration on the fibril structure of the matrix:

Using the data of Table 1 and assuming a linear relationship between collagen concentration and the measured properties, predictions of fibril area fraction and matrix stiffness can be determined as a function of collagen concentration using the following equations:

$$\text{Fibril Area Fraction} = 3.6514 \times \text{Collagen Concentration} + 7.3286 \quad R^2 = 0.9681$$

$$\text{Stiffness} = 8.1145 \times \text{Collagen Concentration} - 0.3306 \quad R^2 = 0.9304$$

Prediction of Stiffness as a function of Fibril Diameter (Assumption: fibril area fraction does not change; relationship based upon pH data):

$$\text{Stiffness} = -0.2916 \text{ Fibril Diameter} + 146.02 \quad R^2 = 0.9581$$
(based upon pH data)

In another illustrative embodiment, the three-dimensional engineered matrices contain fibrils with specific characteristics, including, but not limited to, a fibril area fraction (defined as the percent area of the total area occupied by fibrils in a cross-sectional surface of the matrix; i.e., fibril density) of about 7% to about 26%, about 20% to about 30%, about 20% to about 50%, about 20% to about 70%, about 20% to about 100%, about 30% to about 50%, about 30% to about 70%, or about 30% to about 100%.

In yet another embodiment, the three-dimensional engineered matrices have an elastic or linear modulus (defined by the slope of the linear region of the stress-strain curve obtained using conventional mechanical testing protocols; i.e., stiffness) of about 0.5 kPa to about 40 kPa, about 30 kPa to 100 kPa, about 30 kPa to about 10001 kPa, about 30 kPa to about 10000 kPa, about 30 kPa to about 70000 kPa, about 100 kPa to 1000 kPa, about 100 kPa to about 10000 kPa, or about 100 kPa to about 70000 kPa.

In another embodiment the three-dimensional engineered matrices have a fibril area fraction of about 7% to about 26%. In another embodiment the three-dimensional engineered matrices have a fibril area fraction of about 7% to about 15% or about 16% to about 26%. In another embodiment the three-dimensional engineered matrices have a fibril area fraction of about 18.5% to about 25%. In another embodiment the three-dimensional engineered matrices are formed from col-

TABLE 1

Microstructure and Mechanical Properties of Three-Dimensional Purified Collagen Matrices

| Collagen Concentration | Fibril Area Fraction (Density; %) | Stiffness (Linear Modulus; kPa) | Fibril Diameter (confocal reflection microscopy; nm) | Fibril Diameter (scanning electron microscopy, nm) |
|---|---|---|---|---|
| 0.3 mg/ml, pH 7.4 | | 1.54 ± 0.507 | 418 ± 121 | |
| 1 mg/ml, pH 7.4 | 11.5 ± 1.9 | 10.7 ± 1.93 | 446 ± 65 | |
| 1.5 mg/ml, pH 7.4 | 12 ± 1.4 | 8.5 ± 1.65 | 412.63 ± 76 | 115.16 ± 23.18 |
| 2 mg/ml, pH 7.4 | 14.8 ± 4.25 | 16.6 ± 2.68 | 435 ± 61 | 80.8 ± 18.3 |
| 3 mg/ml, pH 7.4 | 18.4 ± 1.9 | 24.3 ± 4.16 | 430 ± 71 | |
| 2 mg/ml, pH 6 | | 1.84 ± 0.701 | 490 ± 96 | |
| 2 mg/ml, pH 7 | | 12.7 ± 1.18 | 469 ± 73 | |
| 2 mg/ml, pH 7.4 | | 16.6 ± 2.68 | 435 ± 61 | |
| 2 mg/ml, pH 8 | | 22.5 ± 3.65 | 421 ± 62 | |
| 2 mg/ml, pH 9 | | 33.0 ± 6.93 | 392 ± 65 | |
| 1.5 mg/ml type I + 0.75 mg/ml type III | 21.5 ± 2.6 | 13.3 ± 1.4 | 385 ± 72 | 87 ± 17 | lagen at concentrations of about 3.2, 3.4, 3.6, 3.8, 4.0, 4.5 or 5.0 mg/ml of collagen, resulting in three-dimensional engineered matrices having a fibril area fraction of about 19%, 19.7%, 20.5%, 21.2%, 22%, 23.8% and 25.6%, respectively.

In yet another embodiment, the three-dimensional engineered matrices have an elastic or linear modulus of about 0.5 to about 40 kPa. In accordance with another embodiment, the three-dimensional engineered matrices have a relatively low elastic or linear modulus of about 0.5 to about 24.0 kPa. In one other embodiment, the three-dimensional engineered matrices have a relatively high elastic or linear modulus of about 25 to about 40 kPa.

In illustrative embodiments, as discussed above, the polymerization reaction for three-dimensional engineered matrices can be conducted in a buffered solution using any biologically compatible buffer system known to those skilled in the art. For example, the buffer may be selected from the group consisting of phosphate buffer saline (PBS), Tris (hydroxymethyl) aminomethane Hydrochloride (Tris-HCl), 3-(N-Morpholino) Propanesulfonic Acid (MOPS), piperazine-n,n'-bis(2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES) and 1,3-bis[tris(Hydroxymethyl)methylamino]propane (Bis Tris Propane). In one embodiment the buffer is PBS, Tris, or MOPS and in one embodiment the buffer system is PBS, and more particularly 10×PBS. In accordance with one embodiment, the 10×PBS buffer at pH 7.4 comprises the following ingredients:
    1.37 M NaCl
    0.027 M KCl
    0.081 M $Na_2HPO_4$
    0.015 M $KH_2PO_4$
    5 mM $MgCl_2$
    55.5 mM glucose
In one embodiment, to create 10×PBS buffers of different pH's, the ratio of $Na_2HPO_4$ and $KH_2PO_4$ is varied. In another embodiment, ionic strength may be adjusted as an independent variable by varying the molarity of NaCl only.

In accordance with one embodiment, for polymerization to form the three-dimensional engineered matrices, the purified collagen or solubilized extracellular matrix components can be pipetted into a plate with wells and the purified collagen or solubilized extracellular matrix components can be allowed to polymerize under any of the conditions described above. For example, a humidified environment at 37° C. for approximately 30 minutes can be used. In an alternative embodiment, the purified collagen or solubilized extracellular matrix components are injected into a host and are polymerized in vivo.

As discussed above, in accordance with one embodiment, cells can be added to the solubilized extracellular matrix components as the last step prior to the polymerization. In another embodiment, cells can be added after polymerization of the engineered ECM-based matrix or of the engineered purified collagen-based matrix. The three-dimensional engineered matrices comprising the cells can be subsequently injected or implanted in a host for use as a tissue graft. In another embodiment, the cells on or within the three-dimensional engineered matrix can be cultured in vitro, for a predetermined length of time, to increase the cell number prior to implantation or injection into a host. In a further embodiment, the cells can be cultured in vitro, for a predetermined length of time, to increase cell number and the cells can be separated from the matrix and implanted or injected into the host in the absence of the three-dimensional engineered matrix.

In still another illustrative embodiment, the three-dimensional engineered matrices can include exogenous glucose and/or calcium chloride in the interstitial fluid of the matrices to promote cell growth. In one embodiment, about 1.0 mM to about 300 mM glucose and about 0.2 mM to about 4.0 mM $CaCl_2$ is included. In one embodiment where purified collagen is used, the purified collagen comprises about 0.1 mg/ml to about 3 mg/ml total purified collagen in about 0.05 to about 0.005N HCl, about 0.07M to about 0.28M NaCl, about 1.3 to about 4.5 mM KCl, about 4.0 to about 16 mM $Na_2HPO_4$, about 0.7 to about 3.0 mM $KH_2PO_4$, about 0.25 to about 1.0 mM $MgCl_2$, and about 2.77 mM to about 166.5 mM glucose. In this embodiment, polymerization of the purified collagen is induced by the addition of a neutralizing solution such as NaOH. For example, a NaOH solution can be added to a final concentration of 0.01N NaOH. In this embodiment, cells are then added and a calcium chloride solution is also added to bring the final concentration of $CaCl_2$ to about 0.4 mM to about 2.0 mM $CaCl_2$. The composition is then allowed to polymerize either in vitro or in vivo to form a three-dimensional engineered purified collagen matrix comprised of collagen fibrils with cells in and/or on the matrix.

In accordance with one embodiment, a kit is provided for preparing three-dimensional engineered matrices. In this embodiment, the kit comprises sterilized components that can be combined to form a three-dimensional engineered matrix comprising collagen fibrils. In one embodiment, cells may constitute a component of the kit. In accordance with one embodiment, the kit comprises a purified collagen composition or a solubilized extracellular matrix component composition, and a polymerization composition. In one embodiment, the kit comprises separate vessels, each containing one of the following components: purified collagen, a phosphate buffer solution, a glucose solution, a calcium chloride solution, and a basic neutralizing solution. In one embodiment, the purified collagen is provided in a lyophilized form and the kit is further provided with a solution of HCl (or other dilute acid including for example, acetic acid, formic acid, lactic acid, citric acid, sulfuric acid, ethanoic acid, carbonic acid, nitric acid, or phosphoric acid) for resuspending the lyophilized collagen.

In another embodiment, the kit comprises a solution comprising solubilized extracellular matrix components, a phosphate buffer solution, a glucose solution, a calcium chloride solution, an acid solution, and a basic neutralizing solution. In one embodiment the polymerization composition comprises a phosphate buffer that has a pH of about 7.2 to about 7.6 and the acid solution is an HCl solution comprising about 0.05N to about 0.005N HCl. In another embodiment, the acid solution is about 0.01N HCl. In one embodiment, the glucose solution has a concentration selected from the range of about 0.2% to about 5% w/v glucose, or about 0.5% to about 3% w/v glucose, and in one embodiment the glucose solution is about 1% w/v glucose. In one embodiment the $CaCl_2$ solution has a concentration selected from the range of about 2 mM to about 40.0 mM $CaCl_2$ or about 0.2 mM to about 4.0 mM $CaCl_2$, or about 0.2 to about 2 mM $CaCl_2$. In one embodiment the kit is provided with a 10×PBS buffer having a pH of about pH 7.4, and comprising about 1.37M NaCl, about 0.027M KCl, about 0.081M $Na_2HPO_4$, about 0.015M $KH_2PO_4$, about 5 mM $MgCl_2$ and about 1% w/v glucose. In another embodiment, kits are provided that comprise three-dimensional, preformed engineered matrices prepared according to any of the methods described herein and wherein the kits comprise any of the components described herein.

The kits can further comprise instructional materials describing methods for mixing the kit reagents to prepare three-dimensional engineered matrices or describing methods for using preformed, three-dimensional engineered matrices. In particular, the instructional materials can provide information regarding the final concentrations and relative proportions of the matrix components that give optimal microenvironmental conditions including fibril microstructure and mechanical properties for a particular cell type or for a particular desired result.

The lyophilized, solubilized extracellular matrix components and the purified collagen prepared by the methods described herein maintain their bioactivity (i.e., the capacity to polymerize and form fibrils in vitro or in vivo and to remodel tissue in vivo). The solubilized extracellular matrix components or purified collagen can be used, for example, for making engineered ECM-based matrices or engineered purified collagen-based matrices for specific tissue graft applications. If the solubilized extracellular matrix components are lyophilized, the lyophilized, solubilized extracellular matrix components are useful commercially for the mass production of solubilized extracellular matrix components (i.e., the components can be lyophilized and stored without loss of bioactivity) for use in making engineered ECM-based matrices. Lyophilized, solubilized extracellular matrix components that retain bioactivity are also useful for the concentration of solubilized extracellular matrix components for preparing engineered ECM-based matrices that require concentration (i.e., higher concentrations) of the matrix components.

The following examples illustrate specific embodiments in further detail. These examples are provided for illustrative purposes only and should not be construed as limiting the invention or the inventive concept in any way.

EXAMPLE 1

Preparation of Lyophilized, Bioactive ECM Composition

Small intestinal submucosa is harvested and prepared from freshly euthanized pigs (Delphi Ind.) as previously disclosed in U.S. Pat. No. 4,956,178. Intestinal submucosa is powderized under liquid nitrogen and stored at −80° C. prior to use. Digestion and solubilization of the material is performed by adding 5 grams of powdered tissue to each 100 ml of solution containing 0.1% pepsin in 0.01 N hydrochloric acid and incubating for 72 hours at 4° C. Following the incubation period, the resulting solubilized composition is centrifuged at 12,000 rpm for 20 minutes at 4° C. and the insoluble pellet is discarded. The supernatant is dialyzed against at least ten changes of 0.01 N hydrochloric acid at 4° C. (MWCO 3500) over a period of at least four days. The solubilized fractionated composition is then sterilized by dialyzing against 0.18% peracetic acid/4.8% ethyl alcohol for about two hours. Dialysis of the composition is continued for at least two more days, with three additional changes of sterile 0.01 N hydrochloric acid per day, to eliminate the peracetic acid. The contents of the dialysis bags are then lyophilized to dryness and stored.

EXAMPLE 2

Preparation of Lyophilized, Bioactive ECM Composition

Small intestinal submucosa was harvested and prepared from freshly euthanized pigs (Delphi Ind.) as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating for 72 hours at 4° C. Following the incubation period, the solubilized composition was centrifuged at 12,000 rpm for 20 minutes at 4° C. and the insoluble pellet was discarded. The supernatant was lyophilized to dryness and stored.

EXAMPLE 3

Preparation of Reconstituted, Bioactive ECM Composition

Immediately prior to use, lyophilized material from Example 2, consisting of a mixture of extracellular matrix components, was reconstituted in 0.01 N HCl. To polymerize the soluble extracellular matrix components into a 3-dimensional matrix, reconstituted extracellular matrix solutions were diluted and brought to a particular pH, ionic strength, and phosphate concentration by the addition of a phosphate buffer and concentrated HCl and NaOH solutions. Polymerization of neutralized solutions was then induced by raising the temperature from 4° C. to 37° C. Various phosphate initiation buffers were used and the pH of the polymerization reaction was controlled by varying the ratios of mono- and dibasic phosphate salts. Ionic strength was varied based on sodium chloride concentration.

Type I collagen prepared from calf skin was obtained from Sigma-Aldrich Corporation, St. Louis, Mo., and dissolved in and dialyzed extensively against 0.01 M hydrochloric acid (HCl) to achieve desired concentrations. Interstitial ECM was prepared from porcine small intestinal submucosa (SIS). SIS was powdered under liquid nitrogen and the powder stirred (5% w/v) into 0.01-M hydrochloric acid containing 0.1% (w/v) pepsin for 72 h at 4° C. The suspension was centrifuged at 12,000×g for 20 min at 4° C. to remove undissolved tissue particulate and lyophilized to dryness. Immediately prior to experimental use, the lyophilized material was redissolved in 0.01 M HCl to achieve desired collagen concentrations. To polymerize the soluble collagen or interstitial ECM components into a 3D matrix, each solution was diluted and brought to the specified pH, ionic strength, and phosphate concentration by the addition of an initiation buffer and concentrated HCl and NaOH solutions. Polymerization of neutralized solutions was induced by raising the temperature from 4° C. to 37° C. Various initiation buffers were used to make final solutions with the properties shown in Table 2. Ionic strength was varied with sodium chloride concentration. The pH of the polymerization reaction was controlled by varying the ratios of mono- and dibasic phosphate salts.

TABLE 2

Table 2: Engineered ECMs representing purified type I collagen or a complex mixture of interstitial ECM components (SIS) were prepared at varied pH (series 1), ionic strength (series 2), and phosphate concentration (series 3).

| Collagen formulations | | | | SIS formulations | | | |
| --- | --- | --- | --- | --- | --- | --- | --- |
| pH | I | $[P_i]$ | [C] | pH | I | $[P_i]$ | [C] |
| Series 1 | | | | | | | |
| 6.5 | 0.16 | 0.01 | 1 mg/ml | 6.5 | 0.16 | 0.01 | 1 mg/ml |
| 7.0 | 0.16 | 0.01 | 1 mg/ml | 7.0 | 0.16 | 0.01 | 1 mg/ml |
| 7.4 | 0.17 | 0.01 | 1 mg/ml | 7.4 | 0.17 | 0.01 | 1 mg/ml |
| 8.0 | 0.17 | 0.01 | 1 mg/ml | 8.0 | 0.17 | 0.01 | 1 mg/ml |
| 8.5 | 0.17 | 0.01 | 1 mg/ml | 8.5 | 0.17 | 0.01 | 1 mg/ml |
| 9.0 | 0.17 | 0.01 | 1 mg/ml | 9.0 | 0.17 | 0.01 | 1 mg/ml |

TABLE 2-continued

Table 2: Engineered ECMs representing purified type I collagen or a complex mixture of interstitial ECM components (SIS) were prepared at varied pH (series 1), ionic strength (series 2), and phosphate concentration (series 3).

| Collagen formulations | | | | SIS formulations | | | |
|---|---|---|---|---|---|---|---|
| pH | I | [P$_i$] | [C] | pH | I | [P$_i$] | [C] |
| Series 2 | | | | | | | |
| 7.4 | 0.06 | 0.02 | 1 mg/ml | 7.4 | 0.06 | 0.02 | 1 mg/ml |
| 7.4 | 0.10 | 0.02 | 1 mg/ml | 7.4 | 0.30 | 0.02 | 1 mg/ml |
| 7.4 | 0.15 | 0.02 | 1 mg/ml | 7.4 | 0.60 | 0.02 | 1 mg/ml |
| 7.4 | 0.20 | 0.02 | 1 mg/ml | 7.4 | 0.90 | 0.02 | 1 mg/ml |
| 7.4 | 0.25 | 0.02 | 1 mg/ml | 7.4 | 1.20 | 0.02 | 1 mg/ml |
| | | | | 7.4 | 1.50 | 0.02 | 1 mg/ml |
| Series 3 | | | | | | | |
| 7.4 | 0.15 | 0.00 | 1 mg/ml | 7.4 | 0.3 | 0.00 | 1 mg/ml |
| 7.4 | 0.15 | 0.01 | 1 mg/ml | 7.4 | 0.3 | 0.02 | 1 mg/ml |
| 7.4 | 0.15 | 0.02 | 1 mg/ml | 7.4 | 0.3 | 0.04 | 1 mg/ml |
| 7.4 | 0.15 | 0.03 | 1 mg/ml | 7.4 | 0.3 | 0.06 | 1 mg/ml |
| 7.4 | 0.15 | 0.04 | 1 mg/ml | 7.4 | 0.3 | 0.08 | 1 mg/ml |
| 7.4 | 0.15 | 0.05 | 1 mg/ml | 7.4 | 0.3 | 0.11 | 1 mg/ml |

[C] represents collagen concentration in mg/ml,
[P$_i$] represents phosphate concentration in M, and
I represents ionic strength in M.

EXAMPLE 4

Three-Dimensional Imaging of Engineered ECM's by Confocal Reflection Microscopy

Solutions of type I collagen or interstitial ECM components were polymerized in a Lab-Tek chambered coverglass and imaged using a BioRad Radiance 2100 MP Rainbow confocal/multiphoton microscope using a 60×1.4 NA oil immersion lens. Optical settings were established and optimized for matrices after polymerization was complete. Samples were illuminated with 488 nm laser light and the reflected light detected with a photomultiplier tube (PMT) using a blue reflection filter. A z step of 0.2 μm was used to optically section the samples. Because the resolution of the z axis is less than that of the x-y plane, the sampling along the z axis may be different from that of the x-y. Images were collected in the range of 10-25 μm from the upper surface of the coverglass.

EXAMPLE 5

Quantification of Fibril Properties from Three Dimensional Images

Quantification of the fibril diameter distribution within engineered extracellular matrices has been conducted on both two- and three-dimensional image sets obtained using electron and confocal microscopy techniques using methods described within Brightman et al., Biopolymers 54:222-234, 2000. More recently, a Matlab program with a graphical user interface was written for measurement of fibril diameters from these images. For three-dimensional confocal images, depth attenuation was corrected by normalizing against a fitted logarithmic curve, after which images were binarized into white and black pixels using a threshold value. Three rectangles were outlined in the x-y plane across each fibril, with one axis aligned with the fibril. Average fibril diameter in each rectangle was calculated as the total white area divided by the rectangle's length. The average diameter of each fibril was taken to be the average of the three measurements, and the average diameter in a given polymerized composition was calculated as an average of all measurements.

Length of fibril per volume was estimated by dividing the total white volume of an image by the average cross-sectional area of fibrils in that image. Due to distortion in the z-plane, the fibril cross-sections in the image could not be assumed circular and calculated from diameter. Rather, the average cross-sectional area was found by expanding the rectangles described above into three-dimensional boxes. The cross-sectional area of a fibril in was found by dividing the total white volume contained in the box by the length of the box's axis aligned with the fibril.

A Matlab program has also been developed to determine fibril density from two- and three-dimensional images. This method involves thresholding and binarizing the image data to discriminate fibrils from the background. The surface area or volume representing fibrils is then quantified and normalized to the surface area or volume of the image.

EXAMPLE 6

Spectophotometry of Extracellular Matrix Polymerization

The time-course of polymerization was monitored in a Lambda 35 UV-VIS spectrophotometer (Perkin-Elmer) equipped with a temperature-controlled, 8-position cell changer as described previously by Brightman et al., 2000.

EXAMPLE 7

Rheometric Measurements of Extracellular Matrices

Mechanical properties of the polymerized compositions were measured using a TA Instruments AR-2000 rheometer. Neutralized collagen or SIS was placed on the peltier temperature-controlled lower plate at 6° C., and the 40-mm parallel-plate geometry was lowered to a 1-mm gap. The temperature was then raised to 37° C. as oscillation measurements were made every 30 seconds at 1 Hz and 5% strain. After polymerization was complete, an oscillation frequency sweep was made at 5% strain, from 0.1 to 3 Hz. A shear creep test was then conducted with a shear stress of 1 Pa for 1000 seconds.

EXAMPLE 8

Preparation of Reconstituted Bioactive Extracellular Matrices

Small intestinal submucosa was harvested and prepared from freshly euthanized pigs (Delphi Ind.) as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating with stirring for 72 hours at 4° C. Following the incubation period, the solubilized composition was centrifuged at 12,000 rpm for 20 minutes at 4° C. and the insoluble pellet was discarded. The supernatant was dialyzed extensively against 0.01 N HCl at 4° C. in dialysis tubing with a 3500 MWCO (Spectrum Medical Industries). Polymerization of the solubilized extracellular matrix composition was achieved by dialysis against PBS, pH 7.4, at 4° C. for about 48 hours. The polymerized construct was then dialyzed against several changes of water at room temperature and was then lyophilized to dryness.

The polymerized construct had significant mechanical integrity and, upon rehydration, had tissue-like consistency and properties. In one assay, glycerol was added prior to polymerization by dialysis and matrices with increased mechanical integrity and increased fibril length resulted.

EXAMPLE 9

Preparation of Extracellular Matrix Threads

Small intestinal submucosa was harvested and prepared from freshly euthanized pigs (Delphi Ind.) as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating for 72 hours at 4° C. Following the incubation period, the solubilized composition was centrifuged at 12,000 rpm for 20 minutes at 4° C. and the insoluble pellet was discarded.

The solubilized extracellular matrix composition (at 4° C.) was placed in a syringe with a needle and was slowly injected into a PBS solution at 40° C. The solubilized extracellular matrix composition immediately formed a filament with the diameter of the needle. If a blunt-tipped needle is used, straight filaments can be formed while coiled filaments can be formed with a bevel-tipped needle. Such filaments can be used as resorbable sutures.

EXAMPLE 10

Lyophilization and Reconstitution of Solubilized Extracellular Matrix Compositions Frozen small intestinal submucosa powder that had been prepared by cryogenic milling was centrifuged at 3000×g for 15 minutes and the excess fluid was decanted. The powder (5% weight/volume) was digested and solubilized in 0.01 N HCl containing 0.1% weight/volume pepsin for approximately 72 hours at 4° C. The solubilized extracellular matrix composition was then centrifuged at 16,000×g for 30 minutes at 4° C. to remove the insoluble material. Aliquots of the solubilized extracellular matrix composition were created and hydrochloric acid (12.1 N) was added to create a range of concentrations from 0.01 to 0.5 N HCl.

Portions of the solubilized extracellular matrix composition were dialyzed (MWCO 3500) extensively against water and 0.01 M acetic acid to determine the effects of these media on the lyophilization product. Aliquots of the solubilized extracellular matrix composition in 0.01 M acetic acid were created and glacial acetic acid (17.4 M) was added to create a range of concentrations from 0.01 to 0.5 M acetic acid. The solubilized extracellular matrix compositions were frozen using a dry ice/ethanol bath and lyophilized to dryness. The lyophilized preparations were observed, weighed, and dissolved at 5 mg/ml in either 0.01 N HCl or water. The dissolution and polymerization properties were then evaluated. The results are shown in Tables 2-6.

TABLE 3

Gross appearance of solubilized extracellular matrix compositions following lyophilization at various hydrochloric acid concentrations.

| [HCl] (N) | Appearance |
| --- | --- |
| 0.01 | Light, fluffy, homogenous, foam-like sheet; white to off-white in color; pliable |
| 0.05 | Slightly wrinkled and contracted, some inhomogeneities in appearance noted, slight brown tint, pliable to slightly friable in consistency |
| 0.10 | Wrinkled, collapsed in appearance; inhomogeneities noted, some regional "melting" noted; significant brown tint; friable |
| 0.25 | Wrinkled, collapsed in appearance; increased inhomogeneities noted, increased areas of regional "melting" noted; significant brown tint; friable |
| 0.50 | Significant collapse and shrinkage of specimen, dark brown coloration throughout; dark brown in color; friable |

TABLE 4

Dissolution properties of solubilized extracellular matrix compositions following lyophilization at various hydrochloric acid concentrations.

| [HCl] (N) Reconstitution Medium | Reconstitution Properties | |
| --- | --- | --- |
| | $H_2O$ | 0.01 N HCl |
| 0.01 | Completely dissolved in 20-30 minutes, pH 4 | Completely dissolved in 20-30 minutes, pH 2 |
| 0.05 | Majority dissolved in 2 hours; slight particulate noted, pH 3-4 | Majority dissolved in 40 minutes; very slight particulate noted, pH 2 |
| 0.1 | Incomplete dissolution | Incomplete dissolution |
| 0.25 | Incomplete dissolution | Incomplete dissolution |
| 0.50 | Incomplete dissolution | Incomplete dissolution |

TABLE 5

Polymerization properties of solubilized extracellular matrix compositions following lyophilization at various hydrochloric acid concentrations.

| [HCl] (N) Reconstitution Medium | Polymerization Properties | |
| --- | --- | --- |
| | $H_2O$ | 0.01 N HCl |
| 0.01 | Polymerized within 20-30 minutes | Polymerized within 10-20 minutes |
| 0.05 | Weak gel noted at 45 minutes; significant lag time in gelling | Polymerized within 20-30 minutes |
| 0.1 | *No Polymerization | *No Polymerization |
| 0.25 | *No Polymerization | *No Polymerization |
| 0.50 | *No Polymerization | *No Polymerization |

TABLE 6

Dissolution properties of solubilized extracellular matrix compositions following lyophilization at various acetic acid concentrations.

| [Acetic Acid] (M) | Reconstitution Properties | |
| --- | --- | --- |
| | Reconstitution in $H_2O$ | Reconstitution in 0.01 N HCl |
| 0.01 | Completely dissolved in 90 minutes, pH 5 | Completely dissolved in 90 minutes, pH 1-2 |
| 0.05 | Near complete dissolution after 90 minutes; small particulate remained, pH 5 | Completely dissolved in 90 minutes, pH 1-2 |

TABLE 6-continued

Dissolution properties of solubilized extracellular matrix compositions following lyophilization at various acetic acid concentrations.

| | Reconstitution Properties | |
|---|---|---|
| [Acetic Acid] (M) | Reconstitution in H$_2$O | Reconstitution in 0.01 N HCl |
| 0.1 | Completely dissolved in 90 minutes, pH 5 | Near complete dissolution in 90 minutes; small particulate, pH 1-2 |
| 0.25 | Completely dissolved in 90 minutes, pH 5 | Completely dissolved in 90 minutes, pH 1-2 |
| 0.50 | Near complete dissolution after 90 minutes; small particulate remained, pH 5 | Completely dissolved in 90 minutes, pH 1-2 |

TABLE 7

Polymerization properties of solubilized extracellular matrix compositions following lyophilization at various acetic acid concentrations.

| [Acetic Acid] (M) Reconstitution | Polymerization Properties | |
|---|---|---|
| Medium | H$_2$O | 0.01 N HCl |
| 0.01 | Polymerized within 5-10 minutes | Polymerized within 5-10 minutes |
| 0.05 | Polymerized within 5-10 minutes | Polymerized within 5-10 minutes |
| 0.1 | Polymerized within 5-10 minutes | Polymerized within 5-10 minutes |
| 0.25 | Polymerized within 5-10 minutes | Polymerized within 5-10 minutes |
| 0.50 | Polymerized within 5-10 minutes | Polymerized within 5-10 minutes |

These results show that lyophilization in HCl and reconstitution of solubilized extracellular matrix compositions in 0.01 N HCl to 0.05 N HCl or in water maintains the capacity of the components of the compositions to polymerize. The results also show that lyophilization in acetic acid maintains the capacity of the components of the compositions to polymerize when the composition is polymerized in water or HCl. The solubility rate is lyophilization from 0.01 N HCl>lyophilization from 0.01 M acetic acid≧lyophilization from water.

EXAMPLE 11

Preparation of Solubilized Submucosa Composition

1 Dissolution: of small intestinal submucosa (SIS) powder in acetic acid with pepsin
  1.1. Preparation of Acetic Acid with Pepsin
    1.1.1. Prepare the desired volume of 0.5 M acetic acid (typically 1 L; this requires 28.7 mL of 17.4 M glacial acetic acid).
    1.1.2. Add the desired mass of pepsin to achieve a 0.1% w/v solution (typically 1 g, if 1 L of acetic acid is used).
    1.1.3. Place the jar containing acetic acid and pepsin on a stir plate and begin mixing.
  1.2. Preparation of Centrifuged SIS Powder
    1.2.1. Place SIS powder in 50 mL centrifuge tubes.
    1.2.2. Centrifuge SIS powder at 3000×g for 15 minutes.
    1.2.3. Open centrifuge tubes, pour off and dispose of supernatant.
    1.2.4. Remove pellets from tubes. Measure out the desired mass to achieve a 5% w/v solution (typically 50 g, if 1 L of acetic acid was used). Previously prepared and frozen material may be used, and excess centrifuged material may be frozen for later use.
    1.3. Add centrifuged SIS pellet material to acetic acid/pepsin solution.
    1.4. Cover and allow it to stir for 72 hours at 4° C.
2. Centrifugation of Dissolved SIS
  2.1. When removed from stirring, the SIS/pepsin solution should appear viscous and somewhat uniform. Pour SIS/pepsin solution into centrifuge jars. Balance jars as necessary.
  2.2. This mixture should be centrifuged at 16,000×g for 30 minutes at 4° C. If using the Beckman model J2-21, use the JIO head at a speed of 9500 rpm.
  2.3. Remove jars of SIS from centrifuge. Pour the supernatant into a clean jar. Be careful not to disturb the pellet, and stop pouring if the SIS begins to appear more white and creamy (this is pellet material).
3. Dialysis of SIS in Water and Hydrochloric Acid
  3.1. Prepare dialysis tubing as follows:
    3.1.1. Use dialysis tubing with MWCO 3500, diameter 29 1 mll.
    Handle dialysis tubing with gloves, and take care not to allow it to contact foreign surfaces, as it may easily be damaged.
    3.1.2. Cut dialysis tubing to the necessary length. (typically, 3 sections of about 45 cm).
    3.1.3. Wet tubing in millipore water, and leave tubing in the water until each piece is needed.
    3.1.4. Do the following with each length of tubing:
      3.1.4.1. Place a clip near one end of the tubing.
      3.1.4.2. Holding the tubing to avoid contact with foreign surfaces, use a pipette to fill the tubing with SIS solution. Each piece of tubing should receive roughly the same volume of SIS (for example, if three lengths of tubing are used, measure one third of the total volume into each).
      3.1.4.3. Place a clip on the open end of the dialysis tubing. Avoid leaving slack. The tube should be full and taut.
      3.1.4.4. Place the filled dialysis tubing in a container of 0.01 M HCl with a stir bar.
      3.1.4.5. Repeat the above steps to fill all lengths of tubing.
    3.1.5. Leave containers to stir at 40° C.
  3.2. Details regarding changing the dialysis in 0.01 M HCl are given below.
    3.2.1. The 0.01 M HCl in the dialysis containers must be changed several times. This should be done as follows:
    3.2.2. After changing the 0.01 M HCl, another change should not be done for at least two hours.

3.2.3. Change the 0.01 M HCl at least 10 times, over a period of at least four days. This assumes a ratio of 200 mL SIS to 6 L of 0.01 M HCl. If a higher ratio is used, more changes may be necessary.

3.2.4. When changing 0.01 M HCl, do not leave dialysis bags exposed in the air or on the counter. Use tongs or forceps to move a dialysis bag directly from one container to another. Dump the first container in the sink, then refill it with millipore water. The dialysis bags can now be placed in the newly filled container while the other container or containers are changed.

4. Sterilization of SIS 4.1. Place dialysis bags of SIS in a solution of 0.18% Peracetic acid/4.8% Ethanol. Leave to stir for two hours (more time may be necessary).

4.2. Translocate dialysis bags to 0.01 M HCl, and continue dialysis as before. Continue for at least 2 days, changing HCl at least 3 times daily.

4.3. When dialysis is complete, dialysis tubing filled with SIS should be removed from the HCl.

4.4. Remove the clips. Cut open one end of the dialysis tubing and pour SIS into a clean jar.

4.5. SIS should be refrigerated until use.

5. Lyophilization of SIS 5.1. Operating the Vertis Freezemobile 5.1.1. Make sure the condenser is free of any water. Ensure that the black rubber collection tubing attached to the bottom of the condenser is plugged. This can be accessed by opening the grate on the front of the lyophilizer.

5.1.2. Close the door of the condenser, the top of the manifold, and all sample ports. If the door of the condenser or the top of the manifold are not forming a good seal apply a small amount of vacuum grease to the rubber contact surfaces.

5.1.3. Turn on the "Refrigerate" switch. The indicator on the front of the lyophilizer will show a light beside "Condenser" and beneath "On." The light beneath "OK" will not illuminate until the condenser is cooled. The condenser temperature is indicated when the digital readout displays "C1."

5.1.4. When the "condenser" indicator light under "OK" is illuminated, on the "Vacuum" switch. The indicator will show a light beside "Condenser" and beneath "On." The light beneath "OK" will not turn on until the chamber is sufficiently evacuated. The chamber pressure is indicated when the digital readout displays "V 1."

5.1.5. The rollers can be used for freezing a coat of material on the inside surface of a jar. To use the rollers, first ensure that the drain tube is plugged. Using 100% Ethanol, fill the roller tank to a level several millimeters above the top of the rollers. Under-filling will cause ineffective cooling while over-filling will allow ethanol to leak into the jars. The temperature of ethanol bath is indicated when the digital readout displays "T1." This bath is cooled when the "Refrigerate" switch is turned on. The "Rollers" switch controls the turning of the rollers, and may be switched off when no jar is on the rollers.

5.2. Lyophilizing SIS 5.2.1. Lyophilization jars, glass lids, and rubber gaskets should be cleaned with ethanol. Allow ethanol to evaporate completely before use. Mid-size jars, lids, and gaskets (3-inch (7.62 cm) diameter) should be used to fit into the roller if using the Vertis Freezemobile Jar lyophilization.

5.2.2. Pipette 75 mL of SIS solution into the lyophilization jar. Place gasket and lid on jar.

5.2.3. Seal the jar by covering the openings with parafilm. Note the small hole on the neck of the lid, which must be covered.

5.2.4. Place the jar of SIS on the lyophilizer rollers for a minimum of 2 hours.

5.2.5. Alternatively, the jar may be placed in a freezer until all material is solid. In a −80° C. freezer, this takes about 30 minutes.

5.2.6. Prepare a spigot on the lyophilizer by inserting a glass cock with the tapered end out. The tapered end of the cock should be coated with vacuum grease.

5.2.7. Remove the jar of SIS from the rollers (or freezer). Place springs on the hooks to hold the jar and lid together. Remove the parafilm and place the neck of the lid of the jar over the cock. Rotate the jar so that the holes in the lid and the cock do not align. The spigot can be rotated so that the jar rests on the top surface of the lyophilizer.

5.2.8. Turn the valve switch so that it points toward the jar of SIS.

5.2.9. More jars may be added to freeze-dry simultaneously, but add jars one or two at a time. Wait until the vacuum pressure falls to a reasonable range (e.g., 200 millitorr) to ensure that the last jar is sealed before adding subsequent jars.

5.2.10. Leave the jars under vacuum for at least 24 hours.

5.2.11. After lyophilization is complete, turn the switch On the spigot to point away from the jar. This will allow air into the jar.

5.2.12. Remove the jar from the cock.

5.2.13. Lyophilized material is not immediately used, it should be stored in a dry environment. Use a large, sealable container with Dri-Rite or another desiccant, and place containers of lyophilized material therein.

6. Rehydration of Lyophilized SIS 6.1. Place lyophilized SIS into a tube or jar.

6.2. Add the desired quantity of liquid (typically 0.01 N HCl) to the container of SIS.

6.3. Mixing may be accelerated by shaking, stirring, etc. Store container under refrigeration until dissolution of SIS is complete.

Sterilization of Solubilized SIS by Dialysis Against Peracetic Acid Containing Solution 1. Dialyze solubilized SIS against a large reservoir containing 0.18% peracetic acid/4.8% ethanol in water. Dialysis time may vary depending upon peracetic acid concentration, dialysis membrane molecular weight cut off, temperature, etc.

2. Transfer dialysis bags aseptically to reservoirs containing 0.01 N HCl. Dialyze extensively to reduce concentration of residual peracetic acid.

3. When dialysis is complete, dialysis tubing filled with solubilized SIS should be removed from the dialysis tank aseptically.

4. Remove dialysis clips and pour or pipette solubilized SIS into a sterile jar.

5. The disinfected solubilized SIS should be stored at 4° C. until use.

Sterilization of SIS by Direct Addition of Peracetic Acid to SIS Solution

1. Add 100% Ethanol and 32 wt % peracetic acid to solubilized SIS to create a solution with final concentration of 0.18% peracetic acid/4.8% ethanol. Stir well and leave for two hours.

2. Place solubilized SIS in aseptic dialysis bags. Dialyze against sterile solution of 0.01 N HCl.

3. When dialysis is complete, dialysis tubing filled with solubilized SIS should be removed from the dialysis tank aseptically.

4. Remove dialysis clips and pour or pipette solubilized SIS into a sterile jar.

5. The disinfected solubilized SIS should be stored at 4° C. until use.

The invention claimed is:

1. A tissue graft composition comprising a three-dimensional, engineered matrix comprising polymerized collagen fibrils wherein the fibril area fraction of the matrix is about 7% to about 26% and wherein the matrix comprises solubilized extracellular matrix components comprising collagen, glycoproteins, proteoglycans, and glycosaminoglycans; and
   wherein the extracellular matrix components have been treated with an acid but have not been digested with an enzyme, and wherein the collagen remains bioactive after treatment with the acid.

2. The composition of claim 1 wherein the fibril area fraction is about 16% to about 26%.

3. The composition of claim 1 wherein the matrix is lyophilized.

4. The composition of claim 1 wherein the matrix is in an aqueous solution.

5. The composition of claim 2 wherein the matrix is in an aqueous solution.

6. The composition of claim 1 in the form of a kit comprising instructional materials for use of the matrix.

7. The composition of claim 6 in the form of a kit wherein the instructional materials include instructions for injection of the matrix into a patient.

8. The composition of claim 6 in the form of a kit wherein the instructional materials include instructions for growth of cells on or within the matrix.

9. The composition of claim 1 wherein the solubilized extracellular matrix components comprise components from vertebrate submucosa tissue.

10. The composition of claim 9 wherein the submucosa tissue is selected from the group consisting of intestinal submucosa tissue, urinary bladder submucosa tissue, and stomach submucosa tissue.

11. The composition of claim 10 wherein the submucosa tissue is delaminated from the tunica muscularis and at least the luminal portion of the tunica mucosa layer of the submucosa tissue.

12. The composition of claim 1 wherein the solubilized extracellular matrix components comprise basement membrane tissue.

13. The composition of claim 1 further comprising cells.

14. The composition of claim 1 wherein the matrix is sterilized.

15. The composition of claim 14 wherein the matrix is sterilized with a peracid.

16. The composition of claim 15 wherein the peracid is peracetic acid.

17. The composition of claim 6 wherein the kit further comprises cells.

18. The composition of claim 1 wherein the collagen is cross-linked with a cross-linking agent.

19. The composition of claim 2 wherein the collagen is cross-linked with a cross-linking agent.

20. The composition of claim 3 wherein the collagen is cross-linked with a cross-linking agent.

21. The composition of claim 4 wherein the collagen is cross-linked with a cross-linking agent.

22. The composition of claim 10 wherein the collagen is cross-linked with a cross-linking agent.

23. The composition of claim 11 wherein the collagen is cross-linked with a cross-linking agent.

24. The composition of claim 13 wherein the collagen is cross-linked with a cross-linking agent.

25. The composition of claim 14 wherein the collagen is cross-linked with a cross-linking agent.

26. The composition of claim 15 wherein the collagen is cross-linked with a cross-linking agent.

27. The composition of claim 16 wherein the collagen is cross-linked with a cross-linking agent.

28. The composition of claim 17 wherein the collagen is cross-linked with a cross-linking agent.

29. The composition of claim 1 wherein the collagen is not cross-linked with a cross-linking agent.

30. The composition of claim 2 wherein the collagen is not cross-linked with a cross-linking agent.

31. The composition of claim 3 wherein the collagen is not cross-linked with a cross-linking agent.

32. The composition of claim 4 wherein the collagen is not cross-linked with a cross-linking agent.

33. The composition of claim 10 wherein the collagen is not cross-linked with a cross-linking agent.

34. The composition of claim 11 wherein the collagen is not cross-linked with a cross-linking agent.

35. The composition of claim 13 wherein the collagen is not cross-linked with a cross-linking agent.

36. The composition of claim 14 wherein the collagen is not cross-linked with a cross-linking agent.

37. The composition of claim 15 wherein the collagen is not cross-linked with a cross-linking agent.

38. The composition of claim 16 wherein the collagen is not cross-linked with a cross-linking agent.

39. The composition of claim 17 wherein the collagen is not cross-linked with a cross-linking agent.

* * * * *

UNITED STATES PATENT AND TRADEMARK OFFICE
CERTIFICATE OF CORRECTION

| | | |
|---|---|---|
| PATENT NO. | : 8,518,436 B2 | Page 1 of 1 |
| APPLICATION NO. | : 11/914606 | |
| DATED | : August 27, 2013 | |
| INVENTOR(S) | : Voytik-Harbin | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 819 days.

Signed and Sealed this
Twenty-third Day of December, 2014

Michelle K. Lee
*Deputy Director of the United States Patent and Trademark Office*